US012076341B2

(12) United States Patent
Shafikhani

(10) Patent No.: US 12,076,341 B2
(45) Date of Patent: Sep. 3, 2024

(54) USE OF APOPTOTIC COMPENSATORY PROLIFERATION SIGNALING VESICLES IN TISSUE REPAIR AND WOUND HEALING

(71) Applicant: Rush University Medical Center, Chicago, IL (US)

(72) Inventor: Sasha Shafikhani, Elmwood Park, IL (US)

(73) Assignee: Rush University Medical Center, Chicago, IL (US)

( * ) Notice: Subject to any disclaimer, the term of this patent is extended or adjusted under 35 U.S.C. 154(b) by 726 days.

(21) Appl. No.: 17/252,782

(22) PCT Filed: Jun. 18, 2019

(86) PCT No.: PCT/US2019/037614
§ 371 (c)(1),
(2) Date: Dec. 16, 2020

(87) PCT Pub. No.: WO2019/246019
PCT Pub. Date: Dec. 26, 2019

(65) Prior Publication Data
US 2021/0260109 A1  Aug. 26, 2021

Related U.S. Application Data

(60) Provisional application No. 62/686,448, filed on Jun. 18, 2018.

(51) Int. Cl.
*A61K 35/13* (2015.01)
*A61K 9/127* (2006.01)
*A61P 17/02* (2006.01)

(52) U.S. Cl.
CPC .............. *A61K 35/13* (2013.01); *A61K 9/127* (2013.01); *A61P 17/02* (2018.01)

(58) Field of Classification Search
CPC ................................ A61K 35/13; A61P 17/02
See application file for complete search history.

(56) References Cited

U.S. PATENT DOCUMENTS

2014/0045751 A1* 2/2014 Blaber ...................... A61P 9/00
514/9.1

FOREIGN PATENT DOCUMENTS

WO       2015052527 A1    4/2015

OTHER PUBLICATIONS

Gupta, K.H. et al. "Apoptosis and compensatory proliferation signaling are coupled by Crkl-containing microvesicles" Dev Cell. Jun. 19, 2017; 41(6): 674-684.e5 (Year: 2017).*
Gupta, K.H. et al. "Apoptosis and Compensatory Proliferation Signaling Are Coupled by Crkl-Containing Microvesicles" Developmental Cell 2017, 41, 674-684 (Year: 2017).*
Adey, A. et al. The haplotype-resolved genome and epigenome of the aneuploid Hela cancer cell line. Nature 500, 207-211 (2013).
Akers, J.C., Gonda, O., Kim, R., Carter, B.S. & Chen, C.C. Biogenesis of extracellular vesicles (EV): exosomes, microvesicles, retrovirus-like vesicles, and apoptotic bodies. J Neurooncol 113 , 1-11 (2013).
Almeida, E.A. et al. Matrix survival signaling: from fibronectin via focal adhesion kinase to c-Jun NH(2)-terminal kinase. J Cell Biol 149, 741-754 (2000).
Bergantinos, C., Corominas, M. & Serras, F. Cell death-induced regeneration in wing imaginal discs requires JNK signalling. Development 137, 1169-1179 (2010).
Bouchard, V. et al. β1 integrin/Fak/Src signaling in intestinal epithelial crypt cell survival: integration of complex regulatory mechanisms. Apoptosis : an international journal on programmed cell death 13, 531-542 (2008).
Braun, F., Bertin-Ciftci, J., Gallouet, A.S., Millour, J., and Juin, P. (2011). Serum-nutrient starvation induces cell death mediated by Bax and Puma that is counteracted by p21 and unmasked by Bcl-x(L) inhibition. PLoS One 6, e23577.
Chiarugi, P. & Giannoni, E. Anoikis: a necessary death program for anchorage-dependent cells. Biochemical pharmacology 76, 1352-1364 (2008).
Chitteti, B.R. et al. CD166 regulates human and murine hematopoietic stem cells and the hematopoietic niche. Blood 124, 519-529 (2014).
Cocucci, E., Racchetti, G. & Meldolesi, J. Shedding microvesicles: artefacts no more. Trends Cell Biol 19, 43-51 (2009).
Cummings, J., Ward, T.H., Ranson, M. & Dive, C. Apoptosis pathway-targeted drugs-from the bench to the clinic. Biochimica et biophysica acta 1705, 53-66 (2004).
Dai, Y. et al. Podocyte-specific deletion of signal transducer and activator of transcription 3 attenuates nephrotoxic serum-induced glomerulonephritis. Kidney international 84, 950-961 (2013).
Danial, N.N. & Korsmeyer, S.J. Cell death: critical control points. Cell 116, 205-219 (2004).
Darby, I.A., Bisucci, T., Hewitson, T.D. & Maclellan, D.G. Apoptosis is increased in a model of diabetes-impaired wound healing in genetically diabetic mice. The international journal of biochemistry & cell biology 29, 191-200 (1997).
Dekel, B. (2016). The ever-expanding kidney repair shop. J. Am. Soc. Nephrol. 27, 1579-1581.
Deng, Q., Sun, J. & Barbieri, J.T. Uncoupling Crk signal transduction by Pseudomonas exoenzyme T. The Journal of biological chemistry 280, 35953-35960 (2005).
Elmore, S. Apoptosis: a review of programmed cell death. Toxicologic pathology 35, 495-516 (2007).
Fan, Y. & Bergmann, A. Apoptosis-induced compensatory proliferation. The Cell is dead. Long live the Cell! Trends Cell Biol 18, 467-473 (2008).
Fan, Y. & Bergmann, A. Distinct mechanisms of apoptosis-induced compensatory proliferation in proliferating and differentiating tissues in the *Drosophila* eye. Dev Cell 14, 399-410 (2008).

(Continued)

*Primary Examiner* — Andrew S Rosenthal
(74) *Attorney, Agent, or Firm* — Barnes & Thornburg LLP

(57) ABSTRACT

Methods of administering apoptotic compensatory proliferation signaling vesicles (AC PS Vs), and pharmaceutical formulations thereof, are described herein. AC PS Vs can be used to promote proliferation of cells in injured or diseased tissues, for example by adding a therapeutically effective amount of APCSVs to the injured or diseased tissue.

17 Claims, 13 Drawing Sheets

(56) References Cited

OTHER PUBLICATIONS

Fan, Y. et al. Genetic models of apoptosis-induced proliferation decipher activation of JNK and identify a requirement of EGFR signaling for tissue regenerative responses in Drosophila. PLoS Genet 10, e1004131 (2014).

Frisch, S.M. & Screaton, R.A. Anoikis mechanisms. Current opinion in cell biology 13, 555-562 (2001).

Fuchs, Y. & Steller, H. Live to die another way: modes of programmed cell death and the signals emanating from dying cells. Nat Rev Mol Cell Biol 16, 329-344 (2015).

George, B., Verma, R., Soofi, A.A., Garg, P., Zhang, J., Park, T.J., Giardino, L., Ryzhova, L., Johnstone, D.B., Wong, H., et al. (2012). Crk1/2-dependent signaling is necessary for podocyte foot process spreading in mouse models of glomerular disease. J. Clin. Invest. 122, 674-692.

Ginestier, C. et al. ALDH1 is a marker of normal and malignant human mammary stem cells and a predictor of poor clinical outcome. Cell stem cell 1, 555-567 (2007).

Goldufsky, J. et al. Pseudomonas aeruginosa exotoxin T induces potent cytotoxicity against a variety of murine and human cancer cell lines. Journal of medical microbiology 64, 164-173 (2015).

Gupta et al., Apoptosis and Compensatory Proliferation Signaling are Coupled by Crkl-Containing Microvesicles, Developmental Cell, 41:6, (2017), pp. 674-684, e1-e5.

Guris, D.L., Fantes, J., Tara, D., Druker, B.J. & Imamoto, A. Mice lacking the homologue of the human 22q11.2 gene CRKL phenocopy neurocristopathies of DiGeorge syndrome. Nat Genet 27, 293-298 (2001).

Ha, H.C. & Snyder, S.H. Poly(ADP-ribose) polymerase is a mediator of necrotic cell death by ATP depletion. Proceedings of the National Academy of Sciences of the United States of America 96, 13978-13982 (1999).

Han, S.W. & Roman, J. Targeting apoptotic signaling pathways in human lung cancer. Curr Cancer Drug Targets 10, 566-574 (2010).

Hehenberger, K., Heilborn, J., Brismar, K. & Hansson, A. Increased lactate production in chronic diabetic wound fibroblasts showing decreased cellular proliferation. Diabetologia 40, A466 (1997).

Hehenberger, K., Heilborn, J.D., Brismar, K. & Hansson, A. Inhibited proliferation of fibroblasts derived from chronic diabetic wounds and normal dermal fibroblasts treated with high glucose is associated with increased formation of I-lactate. Wound repair and regeneration : official publication of the Wound Healing Society [and} the European Tissue Repair Society 6, 135-141 (1998).

Huh, J.R., Guo, M. & Hay, B.A. Compensatory proliferation induced by cell death in the Drosophila wing disc requires activity of the apical cell death caspase Drone in a nonapoptotic role. Current biology : CB 14, 1262-1266 (2004).

International Search Report, issued in PCT/US2019/037614, dated Oct. 1, 2019.

Karlsson, G. et al. The tetraspanin CD9 affords high-purity capture of all murine hematopoietic stem cells. Cell Rep 4,. 642-648 (2013).

Kastelowitz, N. & Yin, H. Exosomes and microvesicles: identification and targeting by particle size and lipid chemical brobes. Chembiochem 15, 923-928 (2014).

Kitanaka, T., Nakano, R., Kitanaka, N., Kimura, T., Okabayashi, K., Narita, T., and Sugiya, H. (2017). JNK activation is essential for activation of MEK/ERK signaling in IL-1beta-induced COX-2 expression in synovial fibroblasts. Sci. Rep. 7, 39914.

Kondo, S., Senoo-Matsuda, N., Hiromi, Y. & Miura, M. DRONC coordinates cell death and compensatory proliferation. Mol Cell Biol 26, 7258-7268 (2006).

Kroemer, G. et al. Classification of cell death: recommendations of the Nomenclature Committee on Cell Death 2009. Cell death and differentiation 16, 3-11 (2009).

Kroin, J.S., Buvanendran, A., Li, J., Moric, M., Im, H.J., Tuman, K.J., and Shafikhani, S.H. (2015). Short-term glycemic control is effective in reducing surgical site infection in diabetic rats. Anesth. Analg. 120, 1289-1296.

Kroin, J.S., Li, J., Goldufsky, J.W., Gupta, K., Moghtaderi, M., Buvanendran, A., and Shafikhani, S.H. (2016). Perioperative high inspired oxygen fraction therapy reduces surgical site infection with Pseudomonas aeruginosa in rats. J. Med. Microbiol. 65, 738-744.

Krysko, D.V., Vanden Berghe, T., D'Herde, K. & Vandenabeele, P. Apoptosis and necrosis: detection, discrimination and phagocytosis. Methods 44, 205-221 (2008).

Amorte, L., Royal, I., Naujokas, M. & Park, M. Crk adapter proteins promote an epithelial-mesenchymal-like transition and are required for HGF-mediated cell spreading and breakdown of epithelial adherens junctions. Mol Biol Cell 13, 1449-1461 (2002).

Lee, C.H., Wu, S.B., Hong, C.H., Yu, H.S., and Wei, Y.H. (2013). Molecular mechanisms of UV-induced apoptosis and its effects on skin residential cells: the implication in UV-based phototherapy. Int. J. Mol. Sci. 14, 6414-6435.

Lee, Y., El Andaloussi, S. & Wood, M.J. Exosomes and microvesicles: extracellular vesicles for genetic information transfer and gene therapy. Hum Mol Genet 21, R125-134 (2012).

Li, F. et al. Apoptotic cells activate the "phoenix rising" pathway to promote wound healing and tissue regeneration. Sci Signal 3, ra13 (2010).

Luo, Z., Kohli, M.R., Yu, Q., Kim, S., Qu, T., and He, W.X. (2014). Biodentine induces human dental pulp stem cell differentiation through mitogen-activated protein kinase and calcium-/calmodulin-dependent protein kinase II path-ways. J. Endod. 40, 937-942.

Mansbridge, J.N. et al. Growth factors secreted by fibroblasts: role in healing diabetic foot ulcers. Diabetes, obesity & metabolism 1, 265-279 (1999).

Michael, A. et al. Exosomes from human saliva as a source of microRNA biomarkers. Oral diseases 16, 34-38 (2010).

Muralidharan-Chari V. et al. ARF6-regulated shedding of tumor cell-derived plasma membrane microvesicles. Current biology: CB 19, 1875-1885 (2009).

Muralidharan-Chari, V., Clancy, J.W., Sedgwick, A., and D'Souza-Schorey, C. (2010). Microvesicles: mediators of extracellular communication during cancer progression. J. Cell Sci. 123, 1603-1611.

Ohse, T., Pippin, J.W., Vaughan, M.R., Brinkkoetter, P.T., Krofft, R.D., and Shankland, S.J. (2008). Establishment of conditionally immortalized mouse glomerular parietal epithelial cells in culture. J. Am. Soc. Nephrol. 19, 1879-1890.

Ophascharoensuk, V. et al. Role of intrinsic renal cells versus infiltrating cells in glomerular crescent formation. Kidney Int 54, 416-425 (1998).

Osteikoetxea, X. et al. Improved characterization of EV preparations based on protein to lipid ratio and lipid properties. PLoS One 10, e0121184 (2015).

Pace, E. et al. Effects of gemcitabine on cell proliferation and apoptosis in non-small-cell lung cancer (NSCLC) cell lines. Cancer chemotherapy and pharmacology 46, 467-476 (2000).

Perez-Garijo, A., Shlevkov, E. & Morata, G. The role of Opp and Wg in compensatory proliferation and in the formation of hyperplastic overgrowths caused by apoptotic cells in the Drosophila wing disc. Development 136, 1169-1177 (2009).

Pirrone, A., Hager, B., and Fleckman, P. (2004). Primary mouse keratinocyte culture. In Epidermal Cells: Methods and Protocols, A. Turksen, ed. (Humana Press), pp. 3-14.

Porter, A.G. & Janicke, R.U. Emerging roles of caspase-3 in apoptosis. Cell death and differentiation 6, 99-104 (1999).

Rahmani, M. et al. The kinase inhibitor sorafenib induces cell death through a process involving induction of endoplasmic reticulum stress. Mol Cell Biol 27, 5499-5513 (2007).

Raposo, G. & Stoorvogel, W. Extracellular vesicles: exosomes, microvesicles, and friends. J Cell Biol 200, 373-383 (2013).

Reed, J.C. (2006). Drug insight: cancer therapy strategies based on restoration of endogenous cell death mechanisms. Nat. Clin. Pract. Oncol. 3, 388-398.

Ryoo, H.D., Gorenc, T. & Steller, H. Apoptotic cells can induce compensatory cell proliferation through the JNK and the Wingless signaling pathways. Dev Cell 7, 491-501 (2004).

Salic, A. & Mitchison, T.J. A chemical method for fast and sensitive detection of DNA synthesis in vivo. Proceedings of the National Academy of Sciences of the United States of America 105, 2415-2420 (2008).

(56) References Cited

OTHER PUBLICATIONS

Schattenberg, J.M., Schuchmann, M. & Galle, P.R. Cell death and hepatocarcinogenesis: Dysregulation of apoptosis signaling pathways. J Gastroenterol Hepatol 26 Suppl 1, 213-219 (2011).

Scholz, M., and Cinatl, J. (2005). Fas/FasL interaction: a novel immune therapy approach with immobilized biologicals. Med. Res. Rev. 25, 331-342.

Schulze-Osthoff, K., Ferrari, D., Los, M., Wesselborg, S., and Peter, M.E. (1998). Apoptosis signaling by death receptors. Eur. J. Biochem. 254, 439-459.

Selvaraju, T.R., Khaza'ai, H., Vidyadaran, S., Abd Mutalib, M.S. & Vasudevan, R. The neuroprotective effects of tocotrienol rich fraction and alpha tocopherol against glutamate injury in astrocytes. Bosn J Basic Med Sci 14, 195-204 (2014).

Shafikhani, S.H. & Engel, J. Pseudomonas aeruginosa type III-secreted toxin ExoT inhibits host-cell division by targeting cytokinesis at multiple steps. Proceedings of the National Academy of Sciences of the United States of America 103, 15605-15610 (2006).

Shafikhani, S.H., Morales, C. & Engel, J. The Pseudomonas aeruginosa type III secreted toxin ExoT is necessary and sufficient to induce apoptosis in epithelial cells. Cellular microbiology 10, 994-1007 (2008).

Shafikhani, S.H., Mostov, K. & Engel, J. Focal adhesion components are essential for mammalian cell cytokinesis. Cell Cycle 7, 2868-2876 (2008).

Spiro, S.G. & Silvestri, G.A. One hundred years of lung cancer. Am J Respir Grit Care Med 172, 523-529 (2005).

Sun, J. & Barbieri, J.T. Pseudomonas aeruginosa ExoT ADP-ribosylates CT10 regulator of kinase (Crk) proteins. The Journal of biological chemistry 278, 32794-32800 (2003).

Sundin, C., Hallberg, 8. & Forsberg, A. ADP-ribosylation by exoenzyme T of Pseudomonas aeruginosa induces an irreversible effect on the host cell cytoskeleton in vivo. FEMS Microbial Lett 234, 87-91 (2004).

Tauro, B.J. et al. Comparison of ultracentrifugation, density gradient separation, and immunoaffinity capture methods for isolating human colon cancer cell line LIM1863-derived exosomes. Methods 56, 293-304 (2012).

Vachon, P.H. Integrin signaling, cell survival, and anoikis: distinctions, differences, and differentiation. Journal of signal transduction 2011, 738137 (2011).

Valentin-Vega, Y.A., Okano, H. & Lozano, G. The intestinal epithelium compensates for p53-mediated cell death and guarantees organismal survival. Cell death and differentiation 15, 1772-1781 (2008).

Verma, R., Venkatareddy, M., Kalinowski, A., Patel, S.R., Salant, D.J., and Garg, P. (2015). Shp2 associates with and enhances nephrin tyrosine phosphorylation and is necessary for foot process spreading in mouse models of podocyte injury. Mol. Cell Biol. 36, 596-614.

Waring, P., and Mullbacher, A. (1999). Cell death induced by the Fas/Fas ligand pathway and its role in pathology. Immunol. Cell Biol. 77, 312-317.

Wei, L., Yang, Y., Zhang, X. & Yu, Q. Cleavage of p130Cas in anoikis. J Cell Biochem 91, 325-335 (2004).

Wisniewski, J.R., Zougman, A., Nagaraj, N. & Mann, M. Universal sample preparation method for proteome analysis. Nature methods 6, 359 (2009).

Wood, S., Sivaramakrishnan, G., Engel, J. & Shafikhani, S.H. Cell migration regulates the kinetics of cytokinesis. Cell Cycle 10, 648-654 (2011).

Wood, S. et al. Chronic alcohol exposure renders epithelial cells vulnerable to bacterial infection. PLoS One 8, e54646 (2013).

Wood, S., Goldufsky, J. & Shafikhani, S.H. Pseudomonas aeruginosa ExoT Induces Atypical Anoikis Apoptosis in Target Host Cells by Transforming Crk Adaptor Protein into a Cytotoxin. PLoS pathogens 11, e1004934 (2015).

Wood, S., Jayaraman, V., Huelsmann, E.J., Bonish, B., Burgad, D., Sivaramakrishnan, G., Qin, S., Dipietro, L.A., Zloza, A., Zhang, C., et al. (2014). Pro-inflammatory chemokine CCL2 (MCP-1) promotes healing in diabetic wounds by restoring the macrophage response. PLoS One 9, e91574.

Wood, S.J., Goldufsky, J.W., Bello, D., Masood, S., and Shafikhani, S.H. (2015b). Pseudomonas aeruginosa ExoT induces mitochondrial apoptosis in target host cells in a manner that depends on its GAP domain activity. J. Biol. Chem. 290, 29063-29073.

Yonehara, S., Ishii, A., and Yonehara, M. (1989). A cell-killing monoclonal anti-body (anti-Fas) to a cell surface antigen co-downregulated with the receptor of tumor necrosis factor. J. Exp. Med. 169, 1747-1756.

Zhao, Y.F. et al. Activation of JNKs is essential for BMP9-induced osteogenic differentiation of mesenchymal stem cells. BMB Rep 46, 422-427 (2013).

Zong, W.X., Ditsworth, D., Bauer, D.E., Wang, Z.Q. & Thompson, C.B. Alkylating DNA damage stimulates a regulated form of necrotic cell death. Genes Dev 18, 1272-1282 (2004).

\* cited by examiner

USE OF APOPTOTIC COMPENSATORY PROLIFERATION SIGNALING VESICLES IN TISSUE REPAIR AND WOUND HEALING

RELATED APPLICATIONS

This application is a National Stage application of International Application No. PCT/US2019/037614, filed Jun. 18, 2019, which claims the benefit of the filing date under 35 U.S.C. § 119(e) of Provisional U.S. Patent Application No. 62/686,448, filed Jun. 18, 2018, the entire contents of both of which are hereby incorporated by reference.

FEDERALLY SPONSORED RESEARCH OR DEVELOPMENT

This invention was made with government support under grant number AI110685 awarded by the National Institute of Allergy and Infectious Diseases. The government has certain rights in the invention.

BACKGROUND

1. Technical Field text

The present disclosure pertains to methods and compositions for increasing cell proliferation, such as to treat injury or disease.

2. Background Information

The statements in this section merely provide background information related to the present disclosure and may not constitute prior art.

In the course of normal tissue turnover in humans, approximately one million cells die every second through a highly regulated process of programmed cell death (PCD), known as apoptosis. Cell death must be swiftly balanced with compensatory proliferation to maintain homeostasis and tissue integrity. Apoptosis, in addition to its role in PCD, has been implicated in triggering compensatory proliferation signaling (CPS), whereby dying cells induce compensatory proliferation in their neighboring cells. To date however, the nature of CPS and its molecular components remain largely unknown.

*Pseudomonas aeruginosa* Exotoxin T (ExoT) induces apoptosis in target epithelial cells is an area of investigation in our laboratory. We have demonstrated that ExoT, by ADP-ribosylating Crkl adaptor protein, disrupts focal adhesion and interferes with integrin/FAK/p130Cas/β-catenin survival signaling, inducing anoikis apoptosis in epithelial cells.

During these studies, we have discovered what we believe to be the mediator of apoptotic CPS. Our data demonstrate that a fraction of apoptotic cells produce and release Crkl-containing microvesicles, (distinct from exosomes and apoptotic bodies), that stimulate proliferation in neighboring cells upon contact. Vesicle formation in apoptotic cells requires Crkl while compensatory proliferation signaling, induced by Crkl-microvesicles, is dependent on JNK activity in recipient bystander cells.

Being a relatively unexplored phenomenon, practical applications of CPS have not been realized.

SUMMARY

In one aspect, a method of promoting proliferation of cells in an injured or diseased tissue is described. The method may include administering a therapeutically effective amount of apoptotic compensatory proliferation signaling vesicles (ACPSVs) to the injured or diseased tissue. The ACPSVs may be purified ACPSVs.

The injured tissue may be one of an epithelial lesion and an epithelial laceration.

The diseased tissue may be a diabetic ulcer.

The ACPSVs may be administered as a topical formulation. The topical formulation is selected from the group consisting of an oil, an ointment, a cream, a milk, a powder, an impregnated pad, a towelette, a solution, a gel, a spray, a foam, an emulsion, a suspension, and a lotion. The topical formulation may be a slow-release gel.

The method may include treating the injured or diseased tissue with a single dose of ACPSVs.

The method may include treating the injured or diseased tissue with multiple doses of ACPSVs.

The method may include administering about 1 picogram to about 100 grams of ACPSVs, or about 10 picograms to about 1 gram of ACPSVs, or about 100 picograms to about 10 milligrams of ACPSVs, or about 1 nanogram to about 1 milligram of ACPSVs, or about 10 nanograms to about 100 micrograms of ACPSVs, or about 100 nanograms to about 10 micrograms of ACPSVs, or about 200 nanograms to about 1 microgram of ACPSVs, or any value in between the endpoints of the recited ranges.

The method may include administering about 0.1 micrograms per square millimeter ($\mu g/mm^2$) to about 10 $\mu g/mm^2$ of ACPSVs to the injured or diseased tissue, or administering about 0.2 $\mu g/mm^2$ to about 8 $\mu g/mm^2$ of ACPSVs to the injured or diseased tissue, or administering about 0.25 $\mu g/mm^2$ to about 5 $\mu g/mm^2$ of ACPSVs to the injured or diseased tissue, or administering about 0.3 $\mu g/mm^2$ to about 3 $\mu g/mm^2$ of ACPSVs to the injured or diseased tissue, or administering about 0.3 $\mu g/mm^2$ of ACPSVs to the injured or diseased tissue, or any value in between the endpoints of the recited ranges.

In another aspect, a pharmaceutical composition for promoting proliferation of cells in an injured or diseased tissue is disclosed. The pharmaceutical composition may include a therapeutically effective amount of apoptotic compensatory proliferation signaling vesicles (ACPSVs) and at least one pharmaceutically acceptable carrier.

The pharmaceutical composition may include purified ACPSVs.

The pharmaceutical composition may include ACPSVs isolated from mouse tissue, rat tissue, primate tissue, or human tissue.

The pharmaceutical composition may include purified ACPSVs isolated from cultured cells.

The pharmaceutical composition may be a topical formulation. The topical formulation may be an oil, an ointment, a cream, a milk, a powder, an impregnated pad, a towelette, a solution, a gel, a spray, a foam, an emulsion, a suspension, or a lotion.

The pharmaceutical composition may include a slow-release gel.

The pharmaceutical composition may contain an amount of ACPSVs effective to treat the injured or diseased tissue with a single dose. In another aspect, the pharmaceutical composition may contain an amount of ACPSVs effective to treat the injured or diseased tissue with multiple doses.

The pharmaceutical composition may include about 1 nanogram to about 10 milligrams of ACPSVs.

The pharmaceutical composition may include about 100 nanograms to about 10 micrograms of ACPSVs.

BRIEF DESCRIPTION OF THE DRAWINGS

In order that the disclosure may be well understood, there will now be described various forms thereof, given by way of example, reference being made to the accompanying drawings, in which:

Hela cells were transfected with Crkl-GFP in the presence or absence of Z-VAD and followed by IF time-lapse videomicroscopy. (FIG. 1A) Selected movie frames of a Crkl-transfected apoptotic cell are shown. This cell releases a Crkl-containing microvesicle, before it becomes PI positive, and the bystander cell initiates mitosis after contacting this vesicle. (FIG. 1B) The percentages of non-apoptotic, apoptotic, and Z-VAD-treated, Crkl-GFP transfected cells producing vesicle is shown. (FIG. 1C) The ability of Crkl-GFP transfected apoptotic cells to produce and release vesicles prior or post PI uptake was assessed by IF time-lapse microscopy and the tabulated results are shown. (For FIGS. 1B and 1C, n≥1115, * p<0.001, $\chi^2$ analysis). (FIGS. 1D and 1E) Cells were transiently transfected with Crkl-GFP, Crkl/R38K-GFP, or ExoT/ADPRT-GFP expression vectors. 17 h after transfection, cells were treated with EdU for 2 h, fixed by 10% TCA, and analyzed for EdU incorporation in untransfected cells surrounding transfected apoptotic cells (identified by cell shrinkage/rounding) or healthy (identified by spread-out morphology). Representative images are shown in (FIG. 1D) and the tabulated data are shown in (FIG. 1E) (n≥3 independent experiments, 10 random fields/experiment, ** p<0.0001, One-way ANOVA).

(FIG. 2A) Hela cells either received 10% serum (Mock) or were induced to undergo apoptosis by serum-starvation in the presence or absence of Z-VAD. 24 h after serum starvation, apoptotic cell death was assessed by flow cytometry and the tabulated results from 3 independent experiments are shown in (FIG. 2B). (*** p<0.001, One-way ANOVA). (FIG. 2C) ACPSVs in the 16K fraction of apoptotic cells were visualized by DIC. (FIG. 2D) Vesicle size distribution was determined and plotted (Mean size±S.D.=1.76±1.04 µm, n=822). (FIG. 2E) Peptides from the cell lysate (CL) and the indicated fractions of serum-starved apoptotic cells were probed for TGS101 (exosome marker) and Crkl (ACPSV marker) by Western blotting. (FIG. 2F) The 16K fractions of healthy (Mock), serum-starved (Apop.) and Z-VAD treated serum-starved (Apop.+Z-VAD) were probed for ACPSV content by Western blotting of Crkl and the results from 6 independent studies were plotted in (FIG. 2G). (* p<0.05,  p<0.01, * p<0.001, One-way ANOVA). (FIG. 2H) The lipid contents of the vesicles in the 16K fractions of the indicated cultures were measured and the tabulated data from 3 experiments are shown. (* p<0.01,  p<0.005, One-way ANOVA). (FIG. 2I) Hela cells were treated with 16K fractions of serum-fed healthy (Mock), serum-starved apoptotic (Apop.), or Z-VAD treated serum-starved (Apop.+Z-VAD) and the proliferation levels were determined by cell count 24 h after treatment. The tabulated data from n≥6 independent experiments are shown as the Mean±S.D. (* p<0.001, One-way ANOVA). (FIG. 2L) Representative images of a vesicle producing cell are shown. (FIG. 2M) Representative images of an apoptotic body-producing cell are shown.

(FIG. 3A) The impact of ACPSVs on JNK1/2 activation (phosphorylation) in recipient Hela cells in the presence and absence of 20 µM JNK-specific inhibitor, SP600125 (SP), was assessed by Western blotting at 30 min and 1 h after treatment with 16K fractions from serum-fed healthy (no ACPSV) or apoptotic (contains ACPSV) HeLa cells. Phospho JNK1/2 (p-JNK1/2) expression levels were normalized to total JNK1/2 protein levels and plotted in (FIG. 3B). Data are shown as Mean±SEM (n=3, *p≤0.05, ** p≤0.01, One-way ANOVA). (FIG. 3C) ACPSVs were probed for phosphorylated and un-phosphorylated JNK1/2. (FIG. 3D) Hela cells were pre-treated with SP or DMSO (0.1%) for 2 h prior to treatment with ACPSV or Mock. Proliferation was determined by measuring total cell counts at the time of treatment (0 h) and 24 h post treatment. Data are shown as Mean±SEM (n=3, * p≤0.05,  p≤0.01, * p≤ 0.001, One-way ANOVA). (FIGS. 3E-3F) Hela cells were treated with JNK1/2-specific siRNA or scrambled control (Mock), 24 h prior to ACPS vesicle treatment. (FIG. 3E) JNK1/2 levels were evaluated by Western blotting in HeLa recipient cells prior to vesicle treatment (0 mins) or 30 or 60 mins after vesicle treatment. (FIG. 3F) The ability of ACPSVs to induce proliferation in control or JNK1/2-depleted Hela cells was evaluated 24 h after vesicle addition by cell counts. The data indicate that JNK function is required in recipient cells to mediate CPS induced by ACPSVs. (n=3, ** p≤ 0.001).

Peptides from the 16K fractions of serum-starved apoptotic Hela cells were analyzed by LC-MS/MS. (FIG. 4A) Some of the notable protein groupings were plotted based on the number of proteins identified in each grouping. The results of LC-MS/MS analyses were further corroborated by evaluating the presence of representative proteins from the aforementioned categories within ACPSVs by Western blotting (FIG. 4B) and by IF microscopy (FIG. 4C).

In FIG. 5, Crkl-containing microvesicles appear to mediate apoptotic compensatory proliferation signaling. Hela cells were transfected with Crkl-GFP and followed by IF time-lapse videomicroscopy. A Crkl-transfected apoptotic cell, identified by cell shrinkage (see dark arrow), formed and released three Crkl-containing vesicles (white arrow), which appear to induce proliferation in a neighboring cell (third arrow) upon contact.

FIGS. 6A-6E illustrate that Crkl is required for vesicle formation in apoptotic cells. Hela cells were transfected with Crkl-GFP, Crkl/R38K-GFP, and ExoT/ADPRT-GFP and apoptosis and CPS were assessed by IF timelapse videomicroscopy. (FIG. 6A) Representative frames of movies of apoptotic Hela cells transfected with the indicated genes are shown. (FIG. 6B) The percentages of vesicle producing apoptotic Hela cells transfected with the indicated genes were tabulated and the results are shown (n≥ 1080,  p<0.001, * p<0.0001, $\chi^2$ analysis). (FIG. 6C) The number of vesicles per apoptotic Hela cells transfected with indicated genes was tabulated (n≥ 1080,  p<0.001, * p<0.0001, $\chi^2$ analysis). (FIG. 6D) A model depicting the proliferation inducing capacity indices (PCIs) of apoptotic cells is shown. (FIG. 6E) PCIs of apoptotic Hela cells transfected with indicated genes were determined by time-lapse microscopy and the tabulated data are shown. (n≥ 1080,  p<0.001, * p<0.0001, ×2 analysis).

FIGS. 7A-7E show that necrotic cell death does not lead to CPS. (FIG. 7A) HeLa cells were treated with either N-methyl N'-nitro-N-nitrosoguanidine (MNNG) for 15 min to induce necrosis or DMSO as control (Mock). 24 hr after MNNG treatment, cytotoxicity was measured by flow cytometry, using viability dye. Representative FACS plots for each group are shown. (FIG. 7B) Tabulated measurements for cytotoxicity are shown as Mean±SEM (n=4/group, * p<0.0001, Student's t-test). (FIGS. 7C-7E) Culture supernatants of necrotic and apoptotic HeLa cells were fractionated by differential centrifugation. (FIG. 7C) The presence of Crkl in the ACPSV-containing fraction (16K) was evaluated by Western blotting. (FIG. 7D) Tabulated measurements of the Crkl levels in 16K fractions of apoptotic cells versus necrotic cells are shown. (n=3, * p=0.0024, Student's t-test). (FIG. 7E) 100 μL 16K fraction of apoptotic (contains ACPSVs) and necrotic Hela cells (no vesicle) were added to adherent Hela cells and were evaluated for their ability to induce compensatory proliferation in adherent Hela cells. Proliferation was assessed by performing total cell counts at the time Hela cells received vesicle (0 h) and 24 h following vesicle treatment. Data shown as Mean±SEM (n=3, * p<0.0001, Student's t-test).

HEK primary cells also produce Crkl-containing vesicles which mediate CPS in other cells. (FIG. 8A) HEK cells were cultured either seeded (Mock) or induced to undergo anoikis apoptosis by culturing them in suspension media in the presence or absence of Z-VAD. (FIGS. 8A-8B) Supernatants from the indicated cultures were fractionated, as in FIG. 2, and their 16K fractions were evaluated for ACPSV production by Western blotting, using Crkl as a marker for vesicles, whose expression from 3 experiments was evaluated by densitometer and plotted below (FIG. 8A) or by lipid content measurements from 3 experiments in FIG. 8B. (n=3, * p≤ 0.05,  p≤ 0.01, * p≤ 0.001, one-way ANOVA). (FIG. 8C) ACPSVs in 16K fraction of apoptotic HEK cells were visualized by DIC. Similar to HeLa and B16 cells, vesicles from apoptotic HEK cells were globular and ranged between 1-1.8 micron in diameter. (FIG. 8D) HEK cells were treated with vesicles (16K fractions) harvested from HEK seeded healthy (Mock) cultures, or HEK grown in suspension media (Apop.), or HEK grown in suspension media in the presence of Z-VAD (Apop.+Z-VAD). 24 h after treatment, the proliferation levels were determined by cell counts and the tabulated data from 3 independent experiments were shown as the Mean±S.D. ( p<0.01, * p≤ 0.001, one-way ANOVA). These data indicate that HEK apoptotic cells also produce Crkl-containing vesicles which stimulate proliferation in adherent HEK cells.

NTS injection in mice results in crescent glomeruli. Sections of kidney glomeruli from the NTS-injected (apoptotic) or control (Mock) mice were stained with H&E, PAS, and Masson's Trichrome. H&E staining of NTS-injected mouse shows a glomerular hypercellularity (asterisks) with early crescent formation within Bowman space (arrow). PAS staining of NTS-injected mouse shows a slight increase of mesangial matrix (asterisks) with a fibrocellular crescent (arrow). Trichrome staining of NTS-injected mouse shows thickening of Bowman's capsule (asterisk) and glomerular fibrosis with a fibrocellular crescent (arrow).

Figure 10:
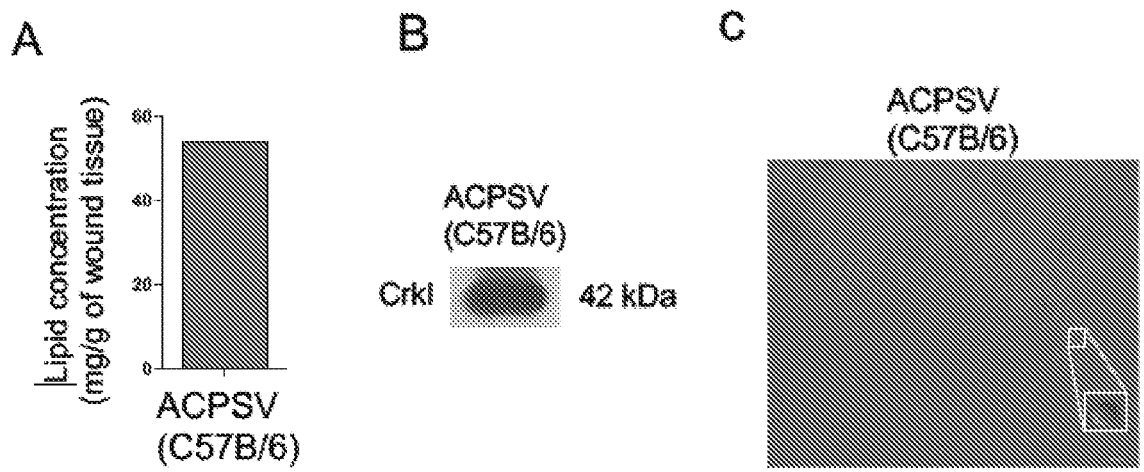

FIGS. 10A-10C are experimental results obtained while analyzing ACPSV purified from skin wounds on day 1 after injury.

FIGS. 10A-10C show a functional analysis of ACPSV purified from skin wounds on day 1 after injury. Wounds were generated on the back skin of C57B/6 mice. ACPSV were purified from wound tissues on day 1 after injury. Vesicle amounts were measured by lipid analysis (FIG. 10A, by Western blotting, or probing for Crkl marker for ACPSVs (FIG. 10B), and by DIC imaging (FIG. 10C).

FIGS. 11A-11E are experimental results showing the result of a wound healing experiment using ASCPVs in mouse as described herein.

Figure 11:
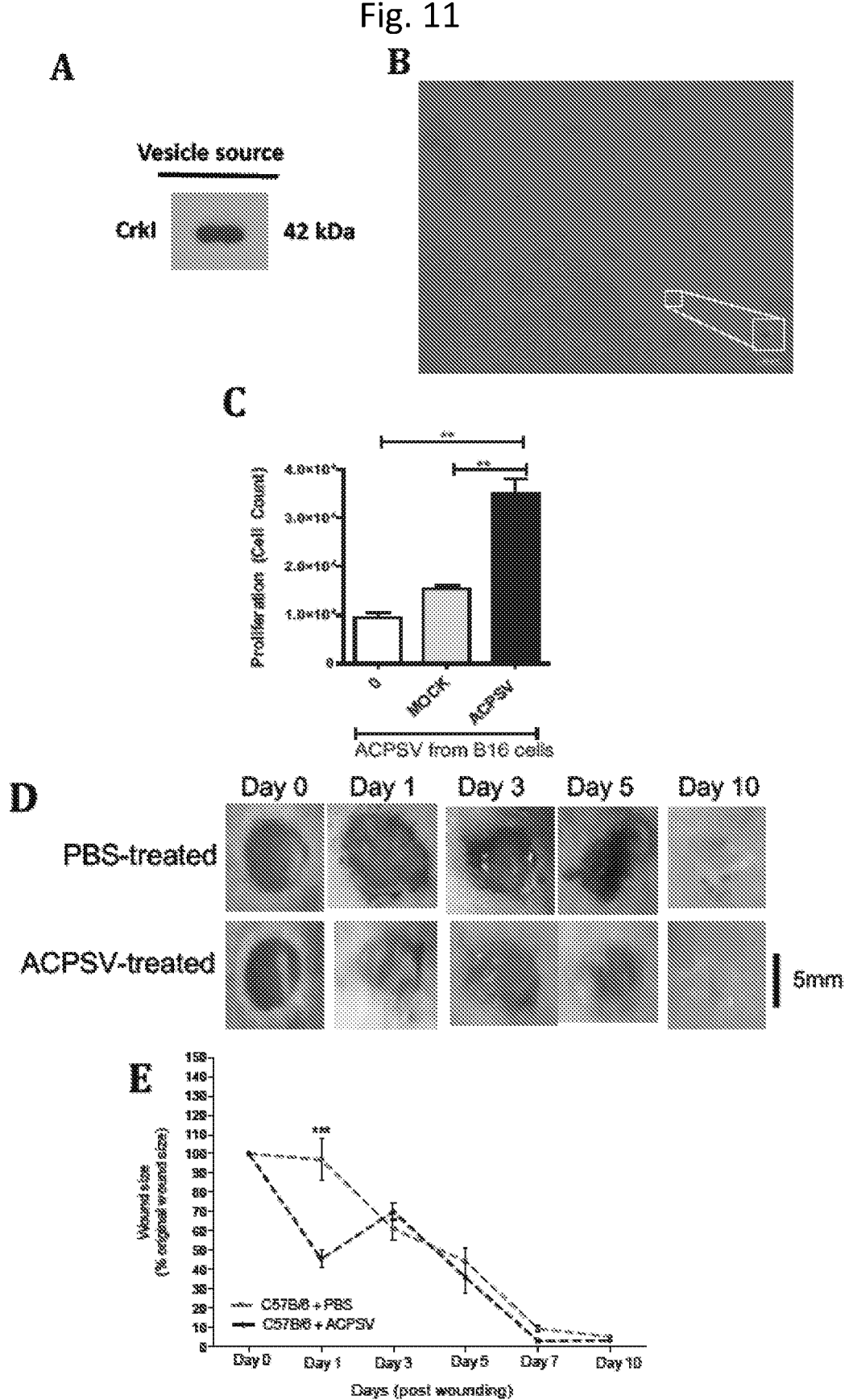

In FIG. 11, ACPSVs stimulate wound healing in C57B/6 mice. ACPSVs were purified from B16 cell culture undergoing apoptosis by differential centrifugation and assessed for vesicle content by Western blotting, using ACPSV marker Crkl (FIG. 11A), by DIC imaging (FIG. 11B), and for their ability to stimulate adherent B16 cells (FIG. 11C). Wounds in C57B/6 mice were treated with either phosphate buffered saline (PBS) or ACPSV (0.3 microgram). Healing was assessed by digital microscopy (FIG. 11D). The tabulated data are shown as Mean±SEM in FIG. 11E. (n=4, *** p≤0.001, two-way ANOVA). Note that one-time treatment with ACPSVs results in a significant, transient healing in a normal wound.

DETAILED DESCRIPTION

The embodiments disclosed below are not intended to be exhaustive or to limit the scope of the disclosure to the precise form in the following description. Rather, the embodiments are chosen and described as examples so that others skilled in the art may utilize its teachings. Unless otherwise defined, all technical and scientific terms used herein have the same meaning as commonly understood by one of ordinary skill in the art to which this disclosure pertains. In case of conflict, the present document, including definitions, will control.

The uses of the terms "a" and "an" and "the" and similar references (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as", "for example") provided herein, is intended merely to better illuminate the disclosure and does not pose a limitation on the scope unless otherwise claimed. No language in the specification should be construed as indicating any non-claimed element as essential to the practice of the embodiments.

As used herein, the term "amount" refers to "an amount effective" or "therapeutically effective amount" of a composition, e.g., ACPSV, to achieve a beneficial or desired prophylactic or therapeutic result, including clinical results. A "therapeutically effective amount" of a composition may vary according to factors such as the disease state, age, sex, and weight of the individual, and the ability of the ACPSV to elicit a desired response in the individual. A therapeutically effective amount is also one in which any toxic or detrimental effects of the administered therapeutic are outweighed by the therapeutically beneficial effects. The term "therapeutically effective amount" includes an amount that is effective to "treat" a subject (e.g., a patient). When a therapeutic amount is indicated, the precise amount of the compositions of the present disclosure to be administered may be determined by a physician with consideration of individual differences in age, weight, tumor size, extent of infection or metastasis, and condition of the patient (subject).

The term "therapeutic effect" as used herein means an effect which induces, ameliorates or otherwise causes an improvement in the pathological symptoms, disease progression or physiological conditions associated with or resistance to succumbing to a disorder, for example a renal disorder, of a human or veterinary patient. The term "therapeutically effective amount" as used with respect to a composition means an amount of the composition which imparts a therapeutic effect to the human or veterinary patient.

The term "dose" means a specified quantity of a pharmaceutical agent provided in a single administration.

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors known in the medical arts. Compositions comprising ACPSVs can be provided topically, by continuous infusion, or by doses at intervals of, e.g., one day, one week, or 1-7 times per week. Doses may be provided intravenously, subcutaneously, topically, orally, nasally, rectally, intramuscular, intracerebrally, or by inhalation. A specific dose protocol is one involving the maximal dose or dose frequency that avoids significant undesirable side effects. A total weekly dose may be at least 0.05 µg/kg body weight, at least 0.2 μg/kg, at least 0.5 μg/kg, at least 1 μg/kg, at least 10 μg/kg, at least 100 μg/kg, at least 0.2 mg/kg, at least 1.0 mg/kg, at least 2.0 mg/kg, at least 10 mg/kg, at least 25 mg/kg, at least 30 mg/kg, at least 40 mg/kg or at least 50 mg/kg (see, e.g., Yang et al, (2003) New Engl. J. Med. 349:427-434; Herold et al, (2002) New Engl. J. Med. 346: 1692-1698; Liu et al, (1999) J. Neurol. Neurosurg. Psych. 67:451-456; Portielji et al, (2003) Cancer Immunol. Immunother. 52: 133-144).

An effective amount for a particular patient may vary depending on factors such as the condition being treated, the overall health of the patient, the method route and dose of administration and the severity of side effects (see, e.g., Maynard et al., (1996) A Handbook of SOPs for Good Clinical Practice, Interpharm Press, Boca Raton, Fla.; Dent (2001) Good Laboratory and Good Clinical Practice, Urch PubL, London, UK).

Methods for co-administration or treatment with a second therapeutic agent, e.g., a cytokine or steroid by way of non-limiting example, are known in the art (see, e.g., Hardman et al., (eds.) (2001) Goodman and Gilman's The Pharmacological Basis of Therapeutics, IO.sup.th ed., McGraw-Hill, New York, N.Y.; Poole and Peterson (eds.) (2001) Pharmacotherapeutics for Advanced Practice: A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.). An effective amount of therapeutic may decrease the symptoms by at least 10%; by at least 20%; at least about 30%>; at least 40%>, or at least 50%.

Additional therapies (e.g., prophylactic or therapeutic agents), which can be administered in combination with the agent described herein may be administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart from the antibodies or fragments thereof of the invention. The two or more therapies may be administered within one same patient visit.

The therapies (e.g., prophylactic or therapeutic agents) of the combination therapies can be administered to a subject concurrently. The term "concurrently" is not limited to the administration of therapies (e.g., prophylactic or therapeutic agents) at exactly the same time, but rather it is meant that a pharmaceutical composition comprising antibodies or fragments thereof of the invention are administered to a subject in a sequence and within a time interval such that the antibodies of the invention can act together with the other therapy(ies) to provide an increased benefit than if they were administered otherwise. For example, each therapy may be administered to a subject at the same time or sequentially in any order at different points in time; however, if not administered at the same time, they should be administered sufficiently close in time so as to provide the desired therapeutic or prophylactic effect. Each therapy can be administered to a subject separately, in any appropriate form and by any suitable route. In various embodiments, the therapies (e.g., prophylactic or therapeutic agents) are administered to a subject less than 15 minutes, less than 30 minutes, less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, 24 hours apart, 48 hours apart, 72 hours apart, or 1 week apart. In other embodiments, two or more therapies (e.g., prophylactic or therapeutic agents) are administered to a within the same patient visit.

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

As used herein, the term "injured tissue" means tissues that have suffered injuries (including destruction and loss of tissues) resulting directly or indirectly from laceration, ulceration, osteoarthritis, bone fracture, cerebral infarction, myocardial infarction, or ischemia. It also means skin, ligament, meniscus, tendon, liver, kidney, esophagus, stomach, lung, and all other tissues that suffered injury.

As used herein, the term "diseased tissue" means tissue derived from a particular organ or tissue type which has a particular class of disease associated with the tissue. Such diseases may include, for example, epithelial diseases, dermal diseases, and complications arising from diabetes including diabetic ulcers. Diseased tissue may also refer to individual cell types such as epithelial cells, stromal cells or stem cells all derived from that diseased tissue.

The term "topical formulation" means a formulation including a drug (in this case, at least ACPSVs) applied to the surface of the body, such as a skin surface including a wounded surface, in the form that can act at or near the location of application. The concentration of the active agent will depend upon the specific agent, the particular disease, the host, the application site.

The present disclosure describes methods of treatment with ACPSVs and pharmaceutical compositions and formulations including ACPSVs.

There may be situations where compensatory proliferation signaling (CPS) could have desirable therapeutic potential. For example, diabetic foot ulcers show decreased proliferative capacity and changes associated with cellular senescence. In this context, CPS vesicles could potentially restore proliferative capacity to these cells and improve healing.

In one aspect, the present disclosure provides a method of using a therapeutically effective amount of isolated or purified ACPSVs to treat injured or diseased tissue. ACPSVs may be purified from any source that will yield the vesicles, such as mouse tissue, rat tissue, primate tissue, human tissue, and others, included wounded tissues of the same.

In one aspect, ACPSVs may be isolated from wound tissues. By way of non-limiting example, wounds may be generated on the back skin of a mouse, such as a C57B/6 mouse. Other sources of wound tissue may be using, including human wound tissue.

In another aspect, ACPSVs may be isolated from cultured cells. Any cell line may be used to produce ACPSVs, including Hela cells, human epithelial keratinocytes (HEKs), and B16 cells.

ACPSVs may be used to treat a number of different wound types. In one aspect, ACPSVs can be administered to a wound of a patient having a dermal or epithelial lesion or laceration to promote proliferation of cells and healing. In another aspect, ACPSVs may be used to promote healing of diabetic ulcers, or other ulcers. ACPSVs may be used in treatment of moisture-associated skin damage, pressure ulcers, abrasions, and deep tissue wounds.

Purified or isolated ACPSVs may be provided as a topical formulation. The vesicles may be suspended in a pharmaceutically acceptable carrier, excipient, or vehicle. The formulation may be in liquid, pasty or solid form, and more particularly in the form of an oil, ointment, cream, milk, powder, impregnated pad, towelette, solution, gel, spray, foam, emulsion, suspension, or lotion. In one aspect, the formulation may be a slow-release gel, which releases the ACPSVs over a course of about 2 days, or about 5 days, or about 7 days, or about 10 days, or about 14 days, or longer. The pharmaceutically acceptable carrier may include but not be limited to such substances as sterile water, olive oil, ethyl oleate, glycols such as propylene glycol, and the like.

In one example, a single dose of 0.3 microgram of ACPSV was sufficient to realize wound healing. ACPSV may be administered in a quantity from about 1 nanogram to about 10 milligrams, or about 5 nanograms to about 1 milligram, or about 10 nanograms to about 100 micrograms, or about 20 nanograms to about 50 micrograms, or about 50 nanograms to about 20 micrograms, or about 100 nanograms to about 10 micrograms, or about 150 nanograms to about 5 micrograms, or about 200 nanograms to about 2 micrograms, or about 300 nanograms to about 1 microgram, or any quantity in between.

A wound to be treated may have a surface area of approximately 20 square millimeters, and 0.3 micrograms (or 300 nanograms) of ACPSVs were applied to the wound. Therefore, healing was observed when ACPSVs were administered at 15 nanograms per square millimeter (ng/$mm^2$). Therapeutically effective doses of topically administered ACPSVs may include from about 0.1 to about 1000 ng/mm$^2$, or about 0.5 to about 500 ng/mm$^2$, or about 1 to about 250 ng/mm$^2$, or about 2 to about 200 ng/mm$^2$, or about 5 to about 100 ng/mm$^2$, or about 10 to about 50 ng/mm$^2$, or about 15 to about 25 ng/mm$^2$, or any value in between.

While transient healing may be observed after a single treatment with ACPSVs, multiple treatments may result in sustained healing. In a prophetic example, a mouse was wounded, opening a wound of about 20 mm$^2$, and treated with 0.3 microgram of ACPSVs every 24 hours. After the first administration, the wound decreased in size by 50%, as in FIG. 11. After the second dose, the wound decreased another 50%, so that it is 25% the original size. After a third dose, the wound decreased another 50%, so that it is 12.5% the original size. As can be seen in FIG. 11, the PBS treated wound is 70% of the original size, but the wound of this prophetic example would decrease to 12.5 the original size.

Results

Figure 5:
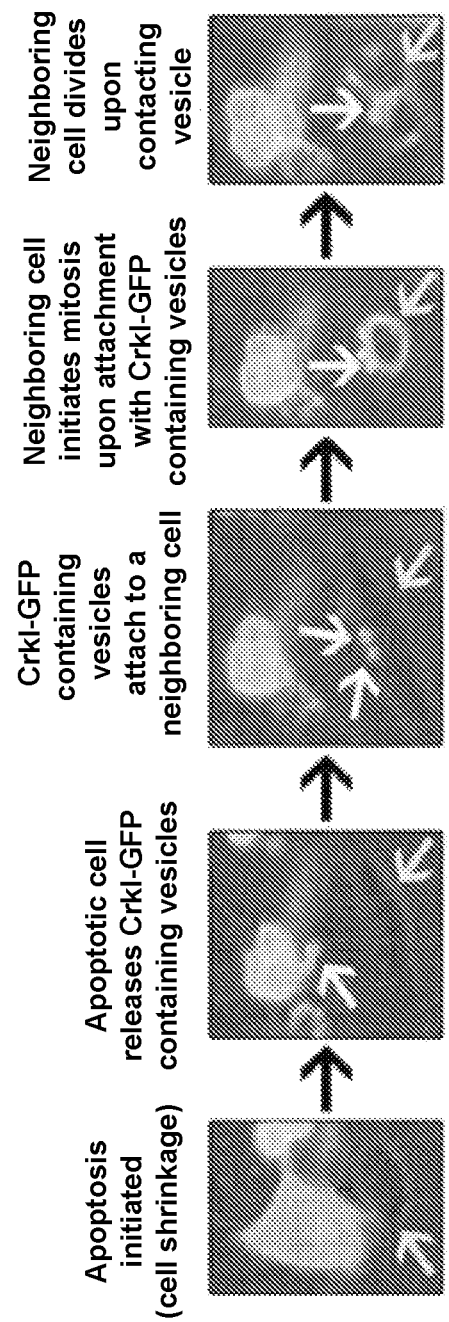
FIG. 5 is a series of photographs illustrating one pathway for proliferation of a bystander cell by contact with an ACPSV as described herein.

Observation of apoptotic CPS. Recently, we reported that the ADP-ribosyltransferase (ADPRT) domain of ExoT—by ADP-ribosylating Crkl adaptor protein-induces anoikis apoptosis in epithelial cells. In one experiment which was designed to examine the role of Crkl in ExoT-induced apoptosis, we found that ~38% of Hela cells transfected with the pIRES2 mammalian expression vector harboring wild-type Crkl-GFP succumbed to apoptosis. During these studies, we made a surprising observation and noted that ~5% of the Crkl-GFP transfected apoptotic cells produced and released 1 to 3 small microvesicles containing Crkl-GFP which induced proliferation in neighboring cells upon contact (FIG. 1A, FIG. 5). After contacting these vesicles, nearly 100% of recipient cells initiated mitosis and proliferated within ~6 h. For simplicity, we will refer to these vesicles as ACPSVs (Apoptotic Compensatory Proliferation Signaling Vesicles).

ACPSVs were not formed or released from healthy Crkl-transfected cells (identified by their spread-out morphology) or when cells, prior to transfection, were pre-treated with Z-VAD, a pan-caspase inhibitor which blocks apoptosis (FIG. 1B), indicating that death signal may be required for vesicle production. Furthermore, these vesicles were primarily produced in cells which had initiated apoptosis (exhibiting cell shrinkage), but prior to their death, as indicated by their negative propidium iodide (PI) staining (FIG. 1C). (The Committee on Cell Death has defined cell shrinkage as an early and reversible step in apoptosis, whereas PI uptake is designated as a late and an irreversible step which indicates cell death in apoptosis).

To further corroborate these data, we transfected Hela cells with Crkl-GFP expression vector and measured the proliferation rates in un-transfected cells (GFP-negative) surrounding healthy Crkl-GFP transfected cells (GFP-positive cells exhibiting spread-out morphology), or apoptotic Crkl-GFP transfected cells (GFP-positive cells exhibiting cell shrinkage/rounding morphology), by EdU incorporation which is a marker for cell proliferation. There was a significant increase in the number of EdU positive (proliferating) un-transfected cells surrounding apoptotic Crkl-GFP transfected cells, as compared to healthy Crkl-GFP transfected cells (FIG. 1D-E), correlating apoptosis with increased proliferation in cells neighboring apoptotic cells.

Although Crkl was contained in these vesicles (FIG. 1A), it remained unclear whether Crkl played any role in CPS or if it was a bystander protein that became trapped in these vesicles as they formed in apoptotic cells. Crkl is a splice variant of the Crk gene which is required for development and for cytokinesis. Since we have only been able to partially deplete Crkl protein in epithelial cells due to its required function in cell proliferation and cytokinesis, we inactivated Crkl by a bacterial toxin and by mutagenesis to assess its possible role in CPS. The ADP-ribosyltransferase (ADPRT) domain of Pseudomonas aeruginosa ExoT inactivates Crkl and interferes with its known functions by ADP-ribosylating a conserved arginine residue in its SH2 domain. Similarly, the arginine (R) to lysine (K) substitution in the SH2 domain of Crkl at position 38 (Crkl/R38K) results in a dominant negative (DN) mutant which also inactivates Crkl and blocks its known activities in a manner that phenocopies ExoT/ADPRT activity. Of note, transient transfection with ExoT/ADPRT or Crkl/R38K also results in apoptosis in epithelial cells.

We transfected Hela cells with Crkl/R38K-GFP, or ExoT/ADPRT-GFP, and measured the proliferation rates in un-transfected cells (GFP-negative) surrounding apoptotic transfected cells by EdU incorporation. All Hela cells transfected with Crkl/R38K-GFP and ExoT/ADPRT-GFP were rounded, whereas only ~35% Hela cells transfected with Crkl-GFP were rounded. This is consistent with the degree of apoptosis induced by these constructs. Importantly, there was a significant reduction in the number of EdU-positive un-transfected cells, surrounding ExoT/ADPRT-GFP and Crkl/R38K-GFP transfected apoptotic cells, as compared to Crkl-GFP transfected apoptotic cells (FIG. 1D-E). These data indicated that Crkl inactivation by ExoT or by Crkl/R38K DN interferes with apoptotic cells' ability to stimulate proliferation in surrounding cells. However, it remained unclear which step(s) of CPS (i.e., vesicle production, vesicle release, vesicle/recipient cell interaction, or vesicle-induced signaling in recipient cell) was blocked by ExoT/ADPRT and Crkl/R38K DN mutant.

Figure 1:
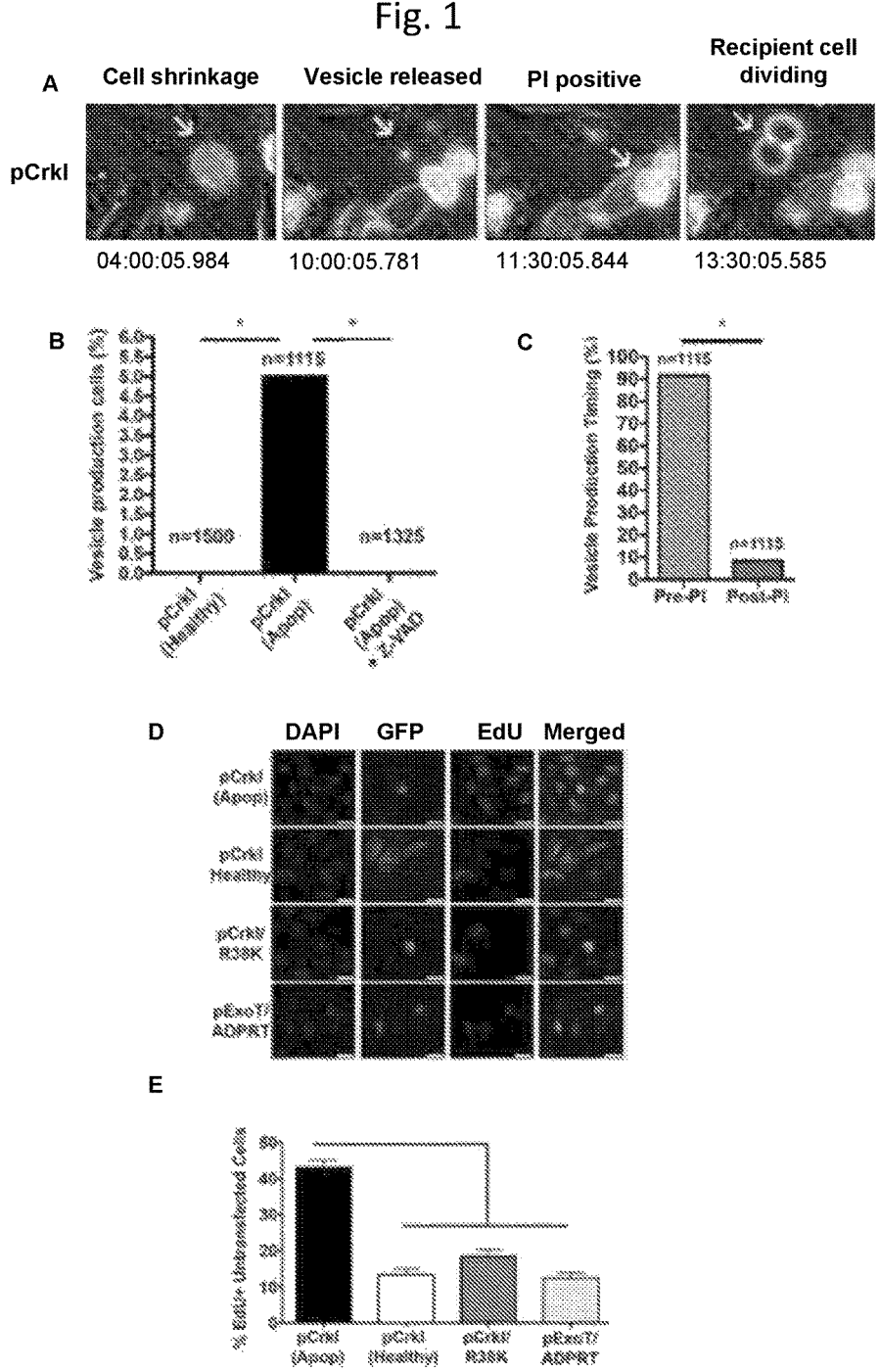
FIGS. 1A-1E illustrate experimental results illustrating that apoptotic cells produce and release Crkl-containing vesicles as described herein.
Figure 6:
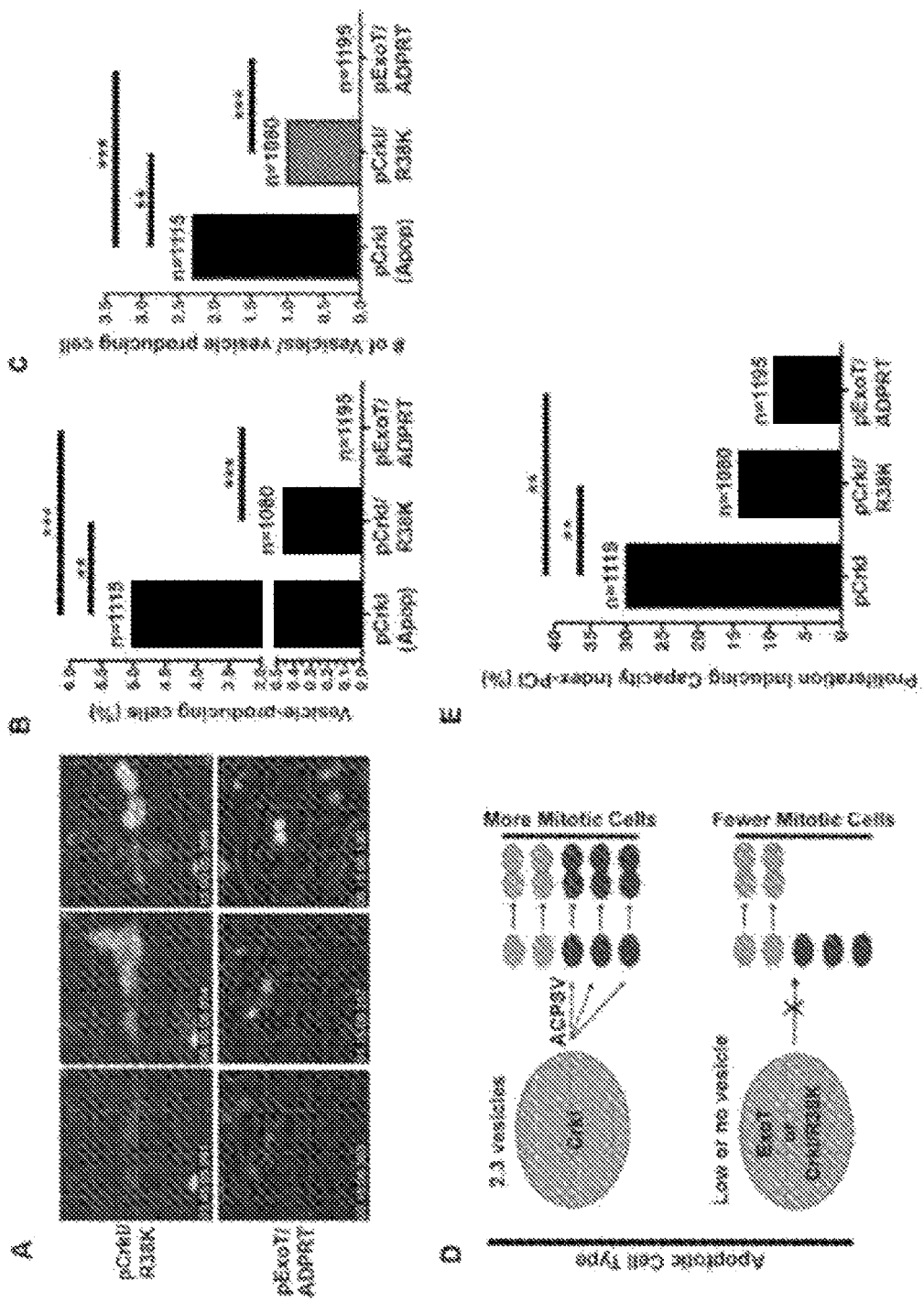
FIGS. 6A-6E are experimental results pertaining to analysis of compensatory proliferation signaling blockage by ExoT/ADPRT and Crkl/R38K DN mutants as described herein.
Figure 7:
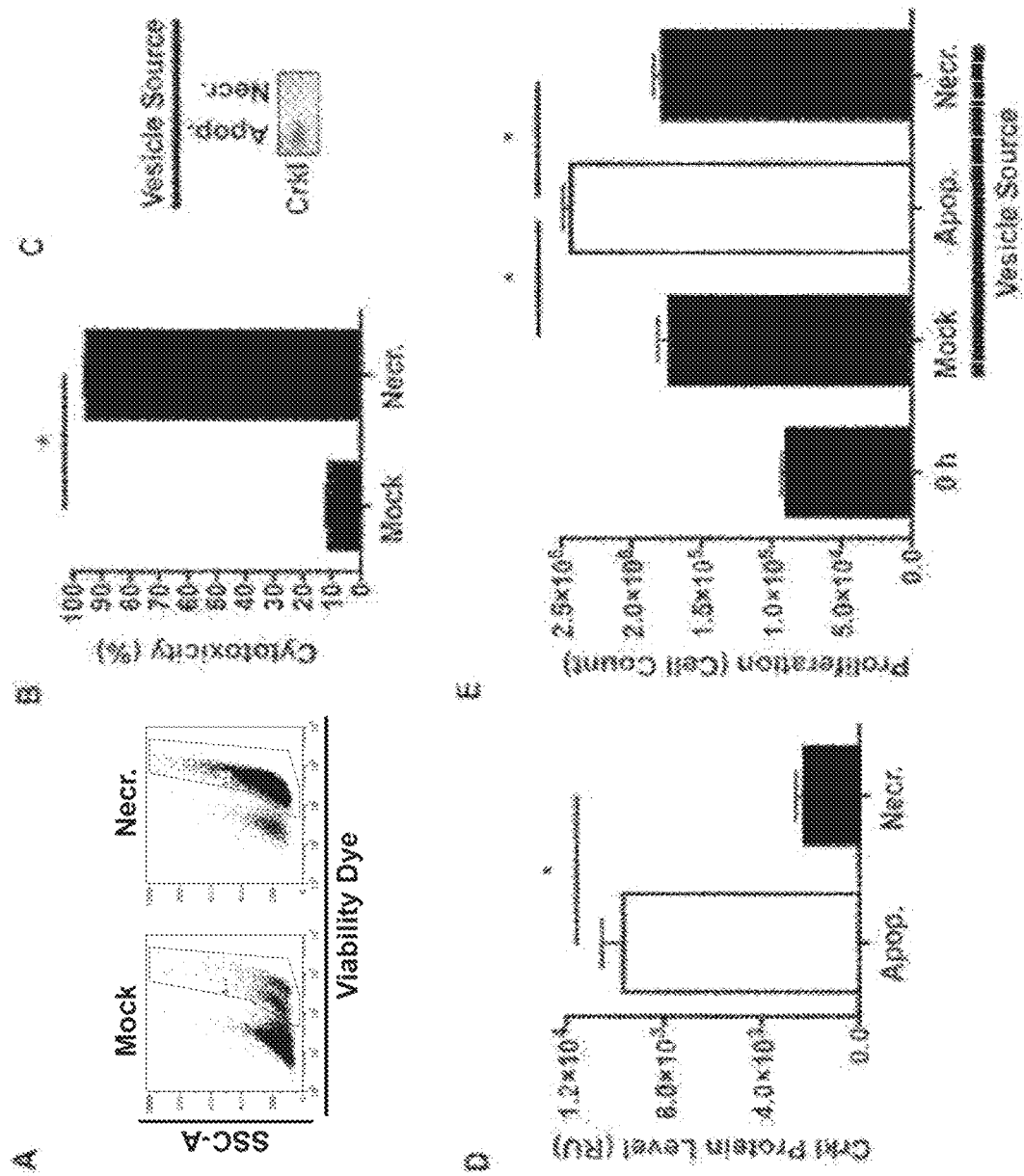
FIGS. 7A-7E are experimental results pertaining to investigations of the relation between necrotic cell death and compensatory proliferation signaling as described herein.
Figure 8:
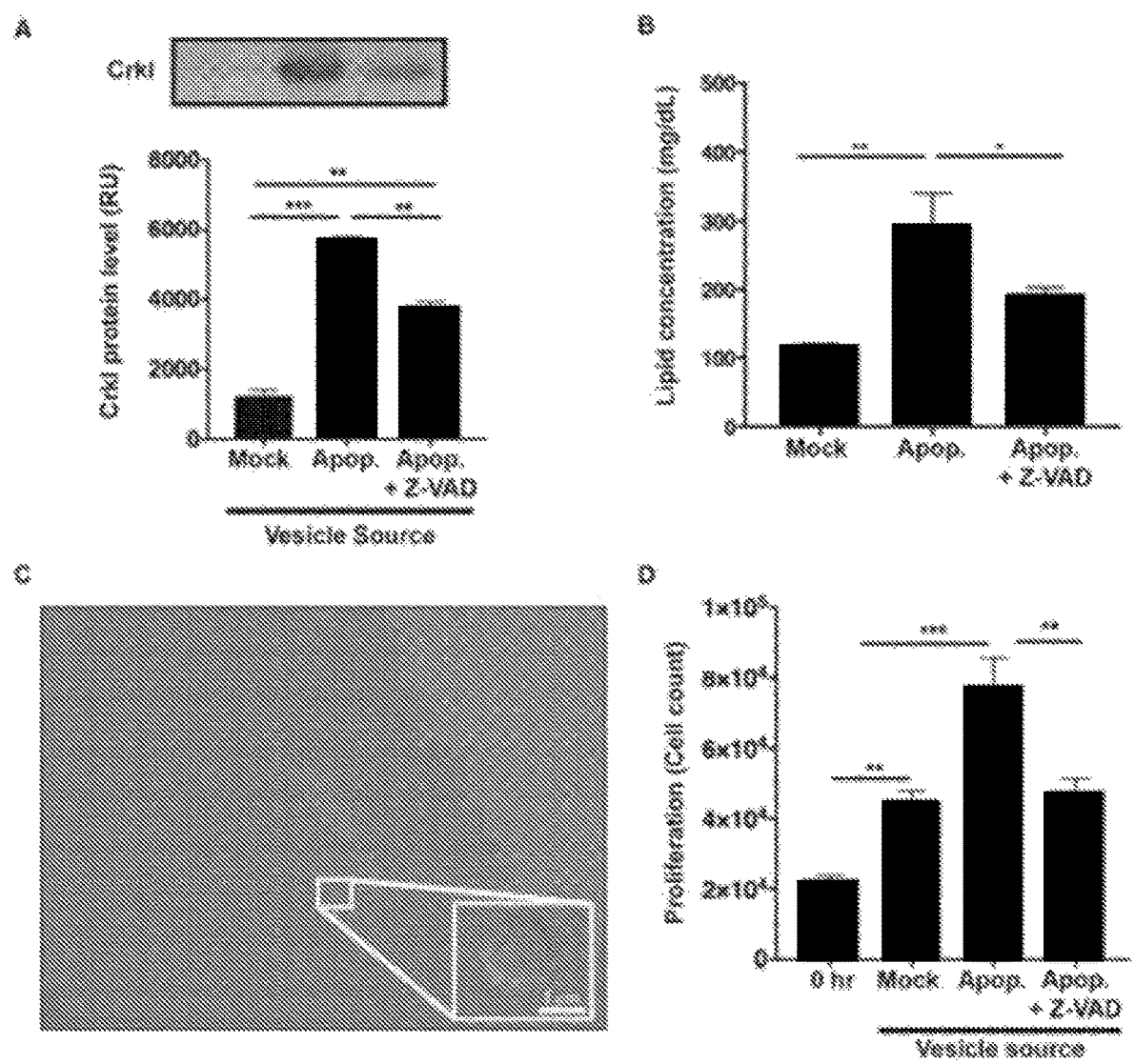
FIGS. 8A-8D are experimental results obtained while investigating vesicle formation in human epithelial kertinaocyte cells (HEK) as described herein.

To assess these possibilities, we repeated these transfection studies and evaluated vesicle formation and release, as well as vesicle interaction with recipient cells, by time-lapse IF videomicroscopy, as we described in FIG. 1. Consistent with our previous report, transfection with Crkl/R38K-GFP or ExoT/ADPRT-GFP resulted in apoptosis in Hela cells (FIG. 6A). However, only 0.5% of Crkl/R38K-GFP transfected apoptotic cells and none of ExoT/ADPRT-GFP cells produced vesicles, as compared to 5.2% of Crkl-GFP transfected apoptotic cells which produced vesicles (FIG. 6B). Moreover, the few Crkl/R38K-GFP transfected cells which produced vesicles, never produced more than one vesicle, as opposed to Crkl-GFP transfected vesicle-producing cells, which on average produced 2.3 vesicles per vesicle-producing cell (FIG. 6C).

To further demonstrate that reduction in vesicle formation in Crkl/R38K or ExoT-transfected apoptotic cells interfered with their ability to induce proliferation in neighboring cells, we determined the proliferation-inducing capacity index (PCI) of the aforementioned transfected apoptotic cells, which we defined as the percentage of proliferating (mitotic) cells in the vicinity of Crkl-GFP, Crkl/R38K-GFP, or ExoT/ADPRT-GFP transfected apoptotic cells (FIG. 6D). In these studies, we included all apoptotic transfected cells, as opposed to only the vesicle-producing apoptotic cells, to account for the reduced vesicle formation in the Crkl/R38K or ExoT-transfected apoptotic cells. Consistent with our hypothesis, the PCIs of Crkl/R38K-GFP and ExoT/ADPRT-transfected apoptotic cells were significantly lower than the PCI of Crkl-transfected apoptotic cells (FIG. 6E). Collectively, these data highlight a role for Crkl in CPS and indicate that Crkl inactivation—by ExoT or by R38K DN mutation—blocks vesicle formation and inhibits CPS in apoptotic cells, thus uncoupling apoptosis from apoptotic CPS.

Figure 2:
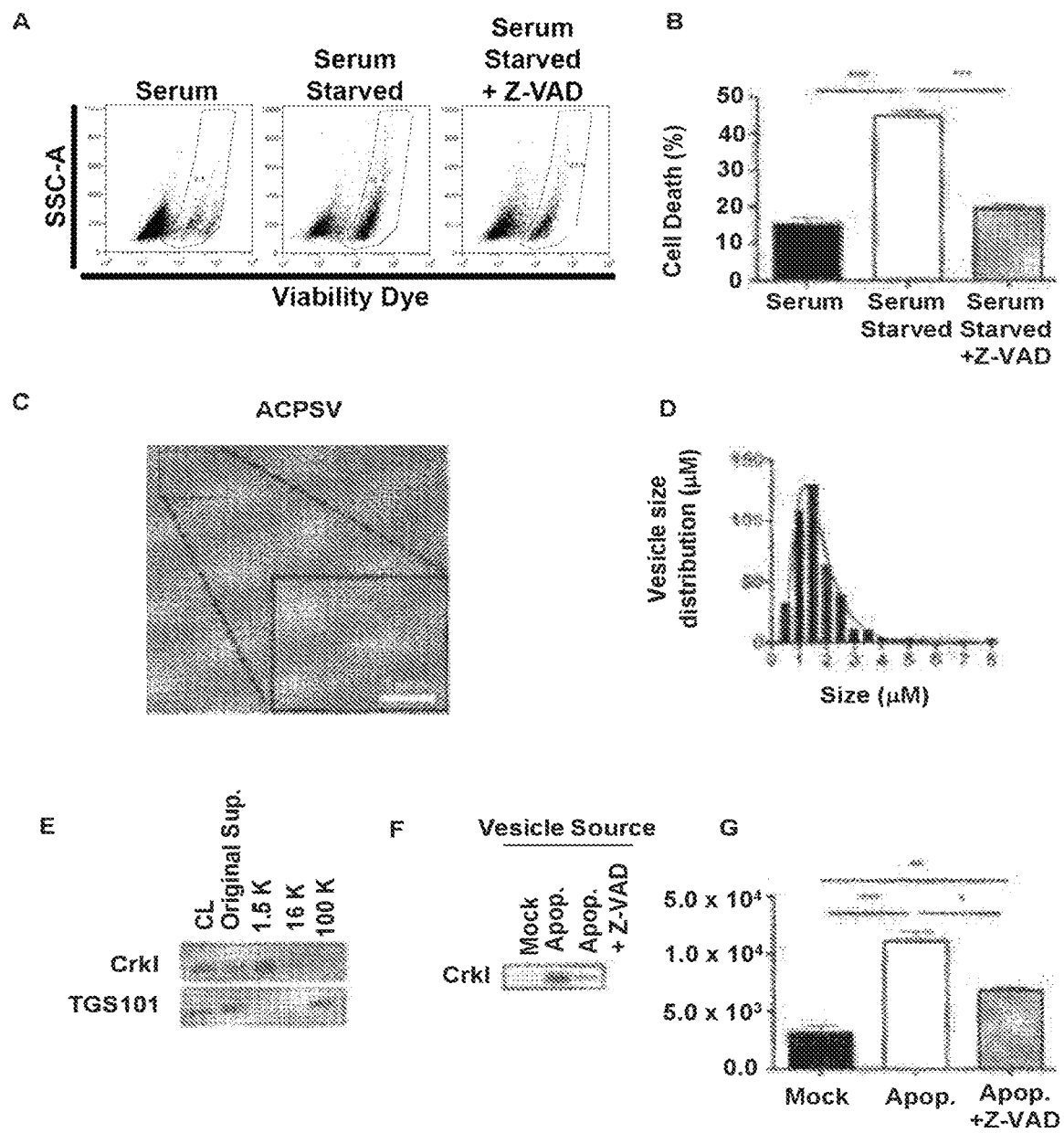
FIGS. 2A-2R illustrate experimental results pertaining to purification and characterization of Crkl-containing microvesicles as described herein.
(FIGS. 2C-2I) Supernatants from the indicated cultures were fractionated by differential centrifugation and evaluated for their Crkl-containing microvesicles (ACPSVs) and CPS.
(FIGS. 2J-2K) The 16K fractions of mock and apoptotic (apop.) Hela cells were passaged through 0.2 u filter to remove vesicle.
(FIGS. 2L-2M) Hela cells were seeded on a coverslip and induced to undergo apoptosis by serum-starvation. 24 h after serum starvation, cells were fixed and analyzed by SEM.
(FIGS. 2N-2O) Original supernatant from serum-starved apoptotic HeLa cell culture was spun down at 100,000×g (100K) to collect all vesicles, which were then added to adherent Hela cells on a coverslip. Five hours after vesicle addition, the fractions of mitotic cells, with no vesicle (NV); with ACPSV only (+AC); with apoptotic body only (+AB); or with a combination of vesicles (+Mix) were assessed by SEM. Selected images representing each group is shown in (FIG. 2N) and the tabulated data from 3 experiments are shown in (FIG. 2O). ( p≤ 0.01, * p≤ 0.001, **** p≤ 0.0001; One-way ANOVA).
(FIGS. 2P-2Q) C57BL/6 mice were injected with nephrotoxic serum (NTS) to induce nephritis or isotype antibody control (Mock). Vesicles were harvested from mock and NTS-injected mice glomeruli and imaged by SEM (FIG. 2P) and evaluated for their Crkl contents by Western blot (FIG. 2Q), and for their ability to induce proliferation in adherent kidney parietal epithelial cells (PECs) in (FIG. 2R). (3 independent experiment, 4 mice/group, each group was done in triplicates, * p<0.05, * p<0.001, * p<0.0001, One-way ANOVA).
Figure 2:
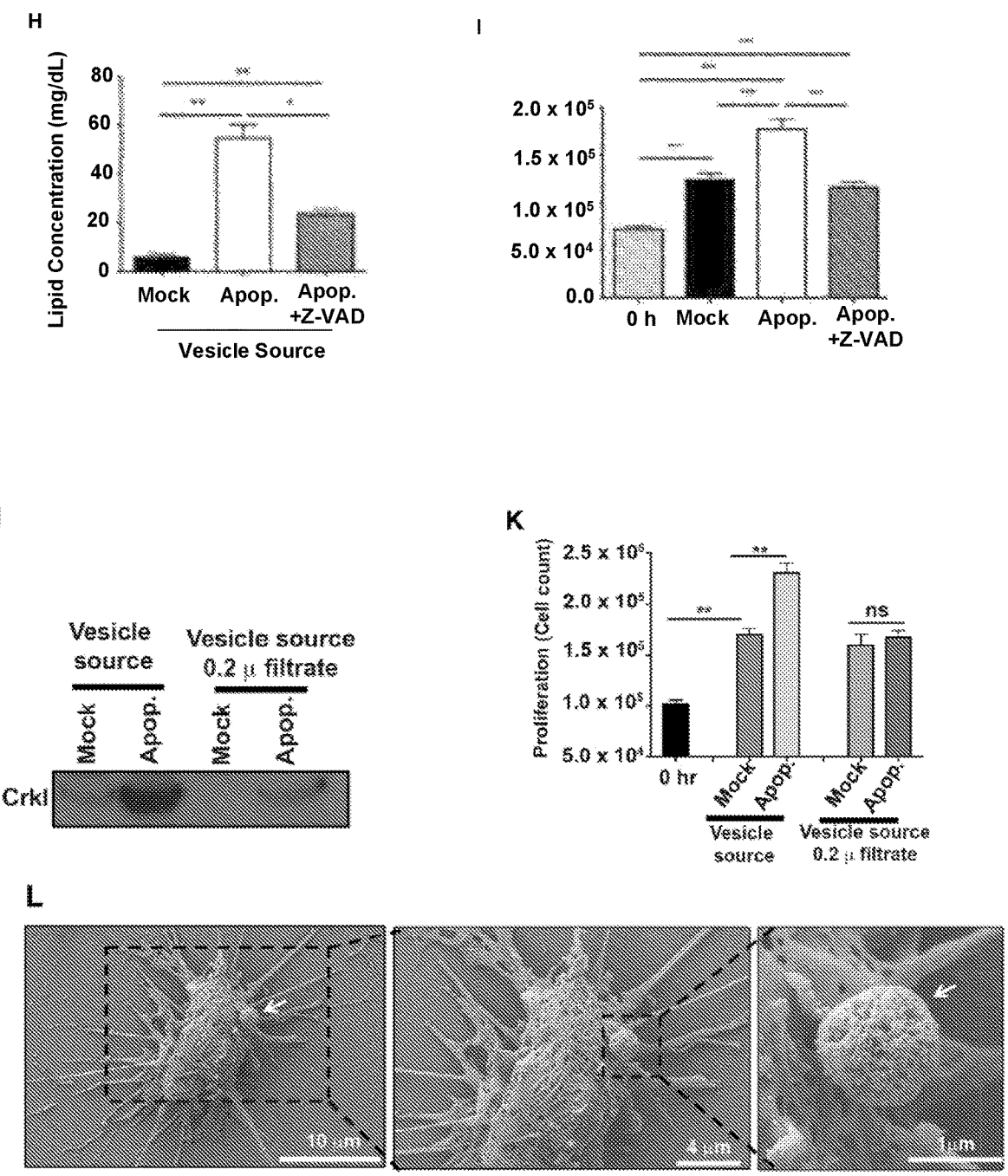
Figure 2:
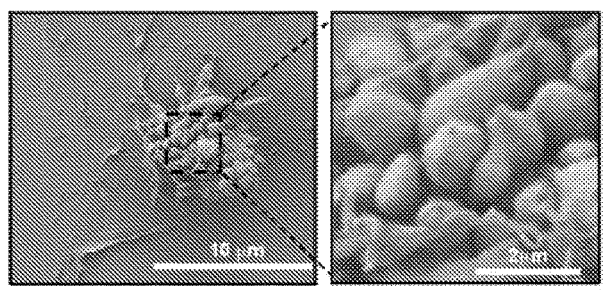
Figure 2:
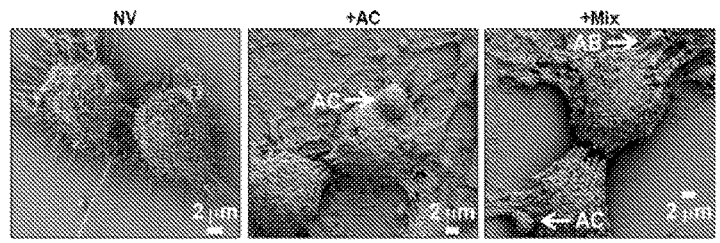
Figure 2:
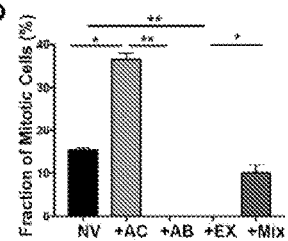
Figure 2:
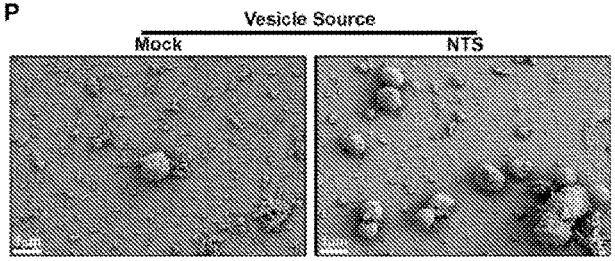
Figure 2:
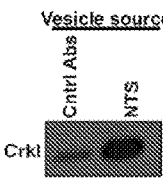
Figure 2:
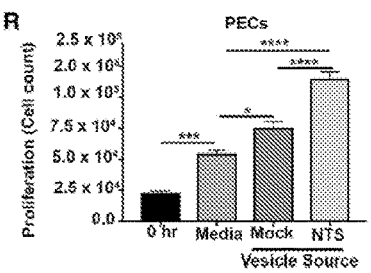

Purification and characterization of Crkl-containing microvesicles (ACPSVs). To ensure that the observed CPS was not an artifact of Crkl overexpression in Hela cells, we tested whether triggering apoptosis by another method would also result in production of Crkl-containing microvesicles capable of inducing compensatory proliferation in neighboring cells. To this end, we induced apoptosis in Hela cells by serum starvation which as expected, caused significant Z-VAD sensitive apoptosis within 24 h (FIG. 2A-B). Supernatants from serum-starved apoptotic and serum-fed healthy (Mock) Hela cells were then collected after 24 h and subjected to differential centrifugation as described in the Experimental Procedure; (Protocol: centrifugation at 1500×g (1.5K) for 5 min followed by passaging through 5-micron filter to remove cell debris and apoptotic bodies, followed by centrifugation at 16,000×g (16K fraction) for 30 min, followed by 100,000×g (100K fraction) for 30 min).

Consistent with the time-lapse videomicroscopy data, microvesicles derived from serum-starved apoptotic cell cultures were globular, as visualized by Differential Interference Contrast (DIC) microscopy (FIG. 2C). These vesicles were distinct from exosomes in that they were primarily found in the 16K fraction as opposed to exosomes that are pelleted at speeds ≥50,000×g, and they were also significantly larger in diameter (1.76±1.04 µm, n=820), than exosomes which are reported to be 40-100 nm in diameter (FIG. 2C-D). Although, the original supernatant (Original Sup.) from apoptotic cells and the 100K fraction contained exosomes—as they probed positive for the exosome marker TGS101—the 16K fraction did not, indicating that 16K fraction was devoid of exosome contamination (FIG. 2E). As expected, Crkl was present in the original supernatant and in the 16K fraction, but not in the 100K exosome fraction (FIG. 2E). Furthermore, 16K fraction from apoptotic cell cultures contained significantly more Crkl-containing vesicles than 16K fractions from healthy (Mock) cell cultures, as assessed by Western blot analyses of their Crkl levels (FIGS. 2F-G), and their lipid content measurements (FIG. 2H).

ACPSVs stimulated proliferation in adherent Hela cells when added exogenously in the media (FIG. 2I). Removing ACPSV vesicles from the 16K fraction by passaging it through 0.2µ filter abrogated its ability to stimulate proliferation in adherent cells, indicating that the vesicles in the 16K fraction of apoptotic cells, but not a soluble factor contaminant in this fraction, are responsible for CPS (FIG. 2J-K). In line with videomicroscopy data, (FIG. 1B), pretreatment with Z-VAD pancaspase inhibitor significantly reduced apoptosis (FIGS. 2A-B), and vesicle production in serum-starved cells (FIGS. 2F-H), and abrogated CPS in recipient cells (FIG. 2I); thus, highlighting the need for cell death signal for vesicle production and CPS.

Hela cells undergoing intrinsic, extrinsic, and anoikis apoptosis—(induced by UV radiation, by anti-Fas antibody, by serum-starvation, or by growth in suspension media—also produced ACPSVs capable of stimulating proliferation in other cells, indicating that other apoptotic programmed cell death can also lead to CPS (data not shown).

We next asked whether under apoptotic conditions, primary cells would also produce ACPSVs capable of stimulating proliferation in other cells. We induced apoptosis in human epithelial keratinocytes (HEK) by growing these cells in suspension media. The 16K fraction from apoptotic HEK cells grown in suspension media also contained Crkl-containing vesicles, which were nearly identical in dimensions to vesicles produced by Hela cells and significantly stimulated proliferation in other HEK adherent cells when added exogenously to the media (FIG. 8A-D). As expected, Z-VAD significantly reduced apoptosis and prevented vesicle formation and CPS in HEK cells grown in suspension media (FIGS. 8A-D). Similarly, mouse epithelial keratinocyte (MEK) primary cells also produced Crkl-containing microvesicles under apoptotic conditions that stimulated proliferation in MEK adherent cells when added exogenously to the media (FIG. 2E-G). These data indicated that CPS is not restricted to transformed cells and it also occurs in primary cells in response to apoptosis. Of note, HeLa cells undergoing necrotic cell death, due to ATP depletion resulting from treatment with 0.5 mM MNNG (N-methyl-N-nitro-N-nitrosoguanidine) did not produce Crkl-containing ACPSVs and failed to induce compensatory proliferation in adherent Hela cells (FIGS. 7A-7E), indicating that necrotic cell death does not lead to CPS.

Characterization of ACPSVs by Scanning Electron Microscopy (SEM).

To gain insights into the ultrastructure of ACPSVs, we seeded Hela cells on coverslips, serum-starved them for 24 h, and analyzed vesicle formation by SEM. We found a number of apoptotic cells (exhibiting cell shrinkage morphology) that appeared to be forming and releasing vesicles (FIG. 2L) that were very similar to the ACPS vesicles with respect to their size we observed in time-lapse videomicroscopy and by DIC imaging (FIG. 1A, FIG. 2C). We did not find vesicle-producing cells in serum-fed healthy Hela cells (Mock), again highlighting the need for apoptosis signal for CPS. Of note, we also found many apoptotic cells exhibiting classical apoptotic bodies, but in contrast to ACPSVs which were globular in shape and had spongy surface textures, apoptotic bodies were irregularly shaped and had smooth surfaces (FIG. 2M). These morphological differences allowed us to unambiguously distinguish ACPSVs from apoptotic bodies.

There remained a possibility that contaminating apoptotic bodies or exosomes in the 16K fraction may be responsible for mediating CPS. To address this possibility, we spun down the original supernatant of serum-starved apoptotic Hela cells, which contained ACPSVs, exosomes, and apoptotic bodies (FIGS. 2C, 2E, & 2M), at 100×g to collect all vesicles. We then added these vesicles to Hela cells seeded on coverslips. Five hours after vesicle addition, we fixed the cells, imaged them by SEM, and determined the fractions of proliferating (mitotic) cells with no vesicle (NV), those with ACPSV only (+AC), those with apoptotic bodies only (+AB), those with exosomes only (+EX), and those that had more than one type of vesicle (Mix), based on vesicle size and vesicle surface characteristics. Of note, 37.5% of mitotic cells were not included in these analyses because they could not be scored unambiguously due to image distortion resulting from sample preparation for SEM. Importantly, majority of proliferating (mitotic) cells had either ACPSV alone (36.5%) or both ACPSV and apoptotic body (10.5%) associated with their membranes (FIG. 2N-O). In contrast, there were no mitotic cells that had only apoptotic bodies alone (+AB) or exosomes alone (+EX) and ~15.5% of mitotic cells had no vesicles (NV) associated with their membranes (FIG. 2N-O). These data correlated interaction with ACPSV, but not exosomes or apoptotic bodies, with increased proliferation.

Characterization of apoptotic CPS in vivo. To investigate apoptotic CPS in vivo, we used the nephrotoxic serum (NTS)-induced glomerulonephritis animal model. We chose this model because NTS-induced nephritis is characterized by increased apoptosis of glomerular cells, resulting in the formation of crescent glomeruli. Interestingly, NTS nephritis is also characterized with increased proliferation in kidney parietal epithelial cells (PECs) within the crescent glomeruli, suggesting that apoptotic CPS may also be responsible for the enhanced proliferation in these apoptotic crescent glomeruli.

Figure 9:
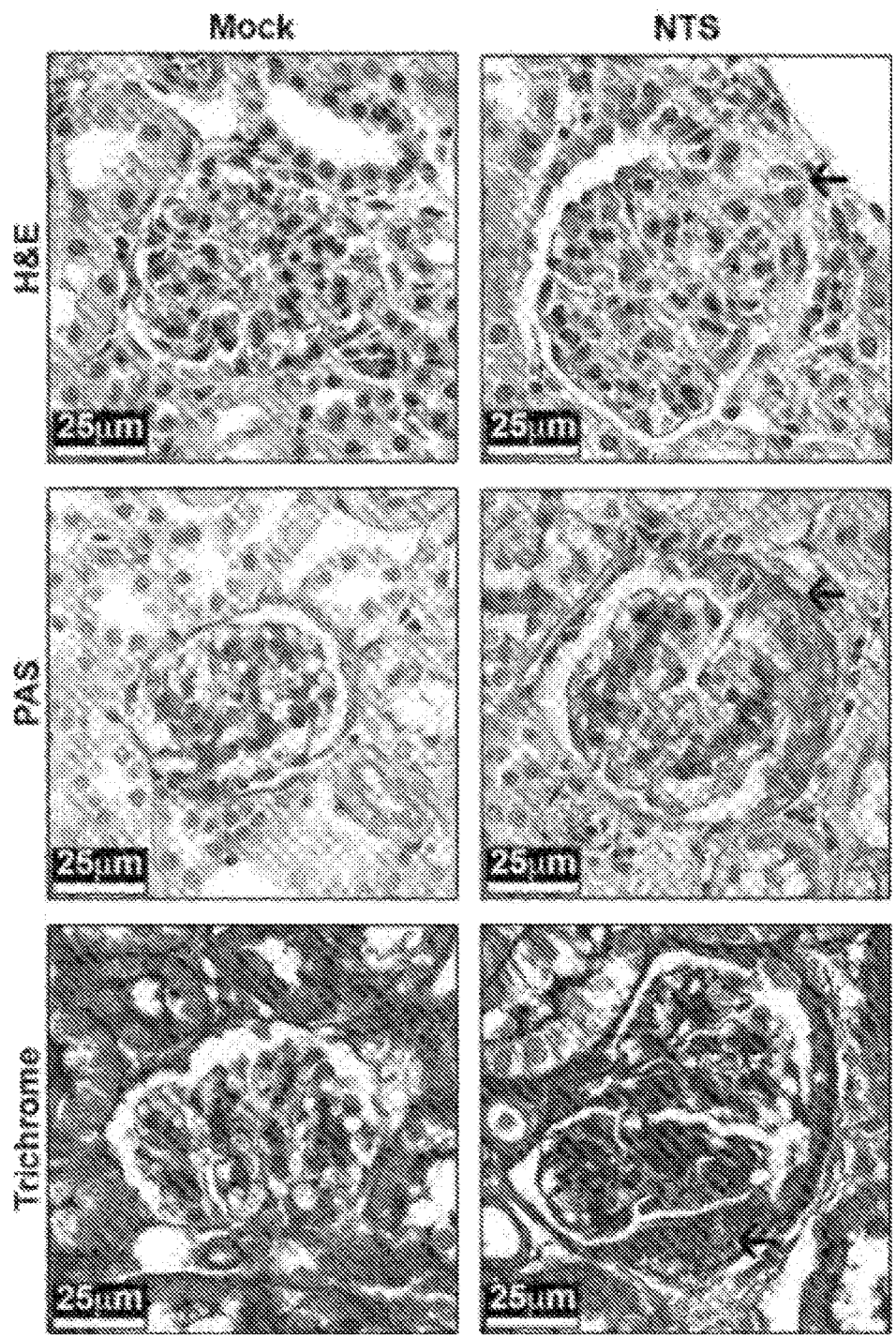
FIG. 9 is a series of photographs of kidney glomeruli as described herein.

To this end, we injected mice with NTS or an isotype antibody (Mock), collected glomeruli at the peak of apoptosis as determined by proteinuria, (~6 days after injection), and evaluated them for crescent formation by hematoxylin and eosin (H&E), Periodic Acid-Schiff (PAS), and Masson's Trichrome histological analyses; for apoptosis by terminal deoxynucleotidyl transferase dUTP nick end labeling (TUNEL) assay; and for proliferation by Ki-67 staining. In line with the previous reports, NTS injection resulted in crescent formation in glomeruli, increased apoptosis, and increased proliferation in crescent glomeruli (FIG. 9). We then assessed the mock and the crescent apoptotic glomeruli for their Crkl-containing ACPSV contents by differential centrifugation. Large microvesicles similar to ACPSV, (0.7-1.7 µm in diameter), were substantially enriched in the NTS-injected crescent glomeruli (FIG. 2P). Vesicles prepared from NTS-injected crescent apoptotic glomeruli contained substantially more Crkl than mock (FIG. 2Q) and were also significantly more effective in inducing proliferation in adherent PECs than vesicles from healthy glomeruli (FIG. 2R). Of note, there were also low-level ACPSV-like large microvesicles in mock-injected glomeruli, which could be due to low-level natural cellular turnover in healthy glomeruli. Cell loss through apoptosis and through urination has been reported in kidney and kidney is known for its remarkable regenerative capacity to replenish and heal. Collectively, these data indicated that vesicle-induced CPS also occurs in vivo in response to apoptosis and it may be an important and immediate response to injury.

Figure 3:
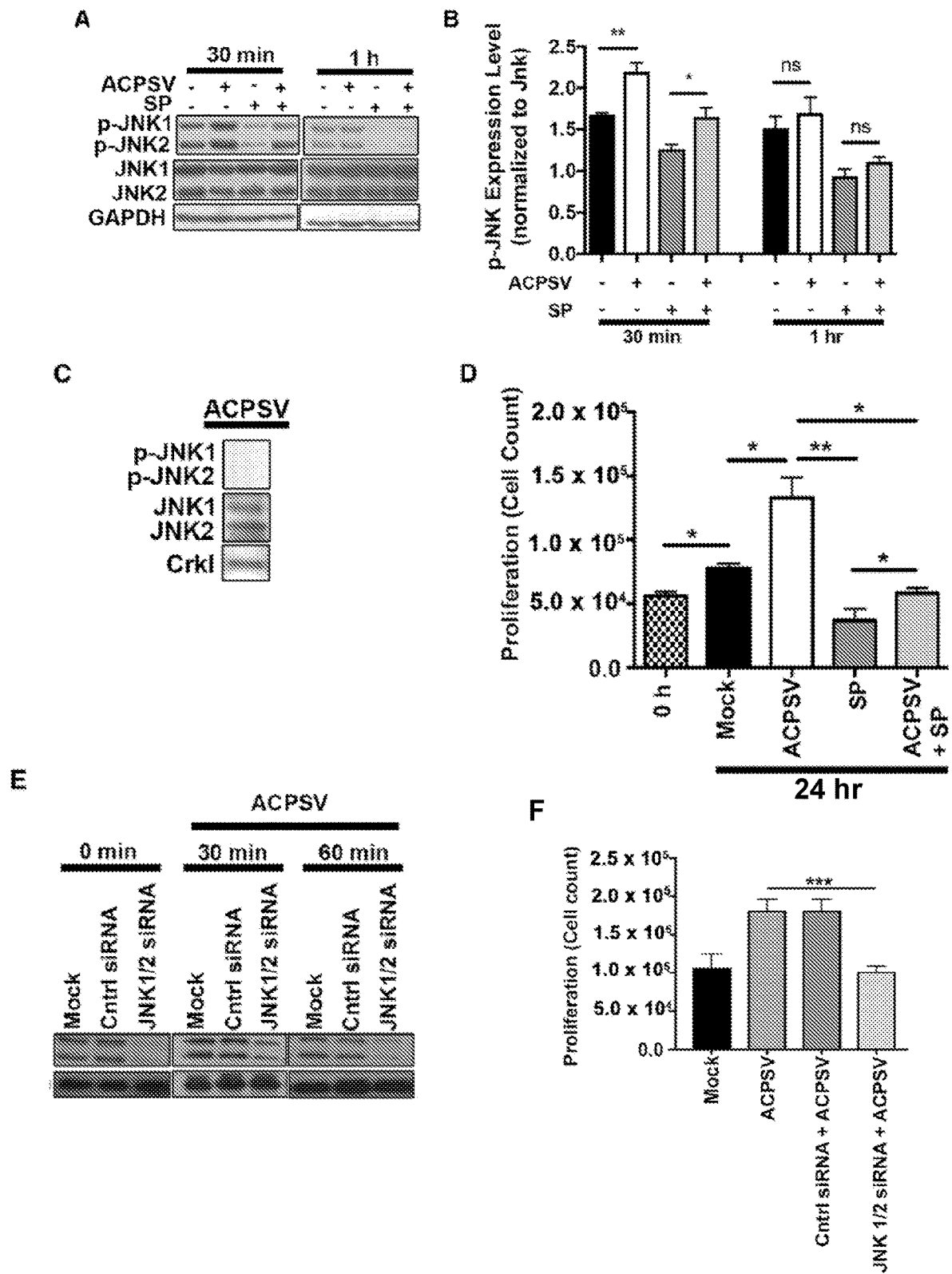
FIGS. 3A-3F illustrate experimental results related to JNK activity and its relation to ACPSV-induced compensatory proliferation in bystander cells as described herein.

Role of JNK in CPS. In *Drosophila*, c-Jun N-terminal kinase (JNK) becomes activated (phosphorylated) in healthy bystander cells neighboring apoptotic cells and JNK activity has been shown to be crucial in mediating CPS in bystander cells. To determine whether JNK played a role in mediating ACPSV-induced proliferation in recipient cells, we first examined the impact of ACPSVs on JNK activation in recipient cells. ACPSVs treatment resulted in transient but significant increases in activated (phosphorylated) forms of JNK1/2 isoforms in recipient Hela cells within 30 min of vesicle treatment but returned to normal levels by 1 h post-treatment (FIG. 3A-B). Although, ACPSVs contained unphosphorylated JNK1/2, they did not contain phosphorylated JNK1/2 (p-JNK1/2), indicating that vesicles were not the source of increased p-JNK1/2 in the recipient cells (FIG. 3C). To assess the requirement for JNK activity in ACPSV-induced compensatory proliferation in recipient cells, we pre-treated Hela cells with JNK-specific inhibitor SP600125 (SP), 2 h prior to vesicle treatment. Pre-treatment with SP inhibited ACPSV-induced JNK activation (FIGS. 3A-B) and significantly reduced ACPSV-induced compensatory proliferation in recipient Hela cells (FIG. 3D). JNK protein depletion in recipient cells by siRNA also abrogated ACPSV-induced proliferation in recipient cells (FIG. 3E-F), ruling out the possibility of off-target effect by SP600125 and indicating that JNK activity in recipient cell is required to mediate proliferation induced by ACPSVs.

Figure 4:
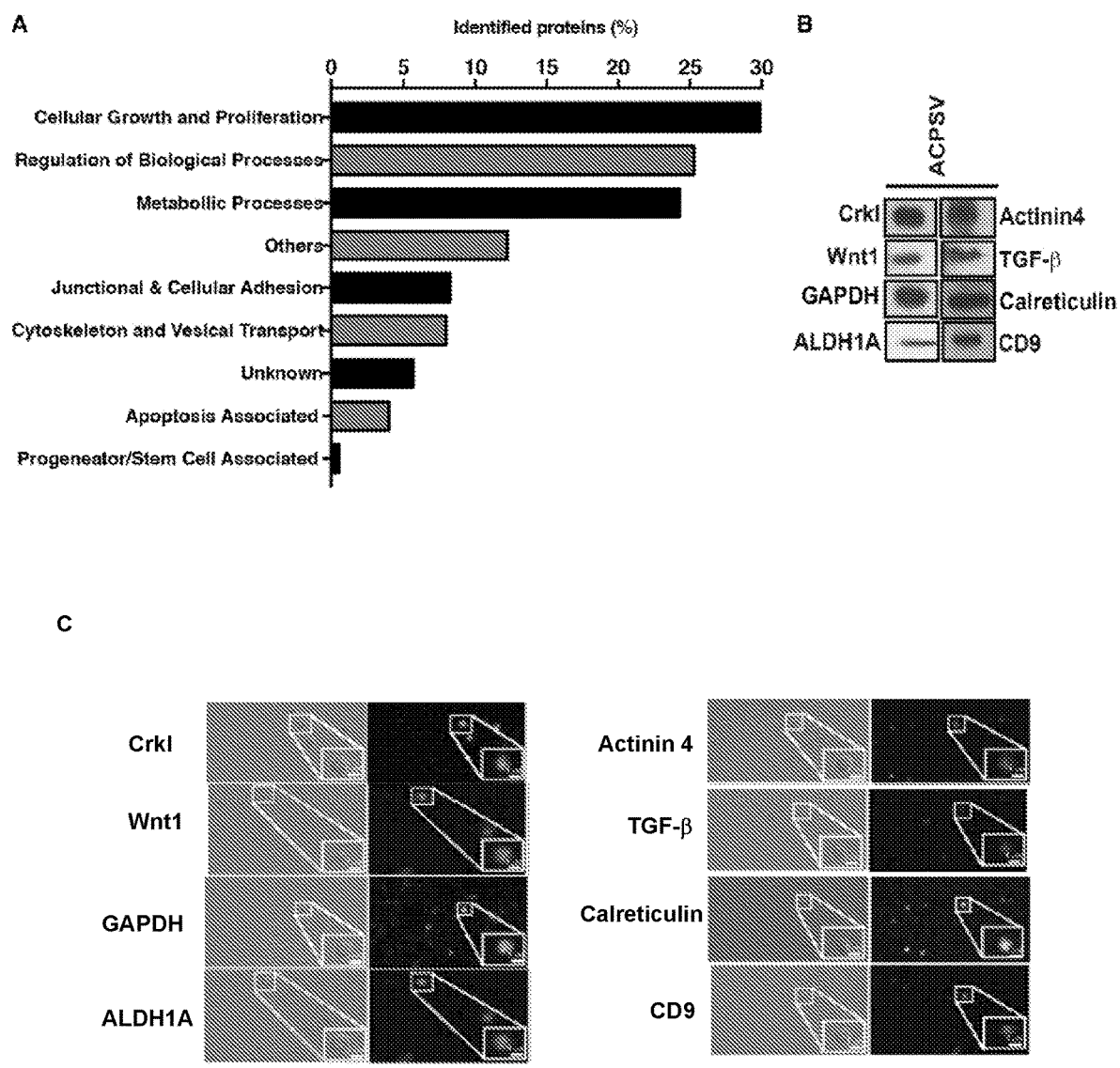
FIGS. 4A-4C illustrate experimental results related to proteomics analyses of ACPSVs as described herein.

Proteomic analyses of ACPSVs. To gain insight into the proteomic content of ACPSV, peptides (~10 µg) extracted from the 16K fraction preparations from two independent experiments, were subjected to proteomics analyses, using the Filter-Aided Sample Preparation Protocol (FASP), as described previously (Wisniewski et al., 2009) and in the Experimental Procedure. Liquid chromatography tandem-mass spectrometry (LC-MS/MS) analyses of ACPSVs identified 2,167 proteins. Of notable proteins found in these vesicles (FIG. 4A), 30.8% have been annotated to function in cellular growth and proliferation processes (e.g., Wnt1, TGF-β1, JNK, Ras, Rac, Crkl); 25.3% in regulation of biological and housekeeping processes (e.g., Elongation factor 2, Protein disulfide-isomerase A3, HSP90); 24.3% in metabolic processes (e.g., GAPDH, Phosphoglycerate kinase, ATP synthetase); 8.25% in junctional and adhesion structures (e.g., Integrin, Vinculin, Profilin-1, Ezrin, Integrin α4); 7.93% in cytoskeletal and transport processes (e.g., Cadherin-1, Actin, Microtubule, Myosin-9, Dynein); 3.96% in apoptosis-associated processes (e.g., Calreticulin, Apoptosis-inducing factor 1, Apoptosis-associated speck-like protein containing a CARD). We corroborated the LC-MS/MS data by evaluating the presence of representative proteins in each category within ACPSVs by Western blotting and by IF microscopy of ACPSVs (FIG. 4B-C).

There is evidence to demonstrate that CPS is mediated by Crkl-containing microvesicles (ACPSVs). We provide visual evidence of CPS and show by live videomicroscopy, SEM imaging, and functional analyses how ACPSVs, (distinct from exosomes and apoptotic bodies), are generated and released from apoptotic cells and how they induce proliferation both in normal and transformed cells upon contact. It is not clear why only ~5% of apoptotic cells have the capacity to produce ACPS vesicles under apoptotic conditions. Intriguingly, ACPSVs contain a number of proteins that have been associated with normal and malignant progenitor and stem cells, such as ALDH1, CD9, CD44, and CD166, as revealed by proteomic analyses. Whether these cells are progenitor or stem-like cells or whether they are yet another unidentified specialized cell type, remains to be determined.

In *Drosophila*, Wingless (Wg; orthologue of mammalian Wnt1), and Decapentaplegic (Dpp; the ortholog of mammalian TGF-β; and bone morphogenic proteins) mitogens, are secreted from apoptotic cells and have been postulated to initiate CPS in bystander cells in a manner that is dependent on bystander cell's JNK activity. Our data reveal that ACPSVs contain Wnt1 and TGF-β mitogens and demonstrate the importance of JNK activity in mediating vesicle-induced CPS in recipient cells, suggesting that ACPS vesicles may be the means by which apoptotic cells deliver mitogens to recipient bystander cells during CPS in *Drosophila*. Future studies are needed to assess the role of ASPS vesicles in mediating CPS in *Drosophila*. Why would vesicles be needed to deliver mitogen(s) to recipient cells? We posit that packaging mitogens in vesicles may increase their effective concentrations upon delivery to recipient cells, by possibly protecting them from proteolysis/degradation and/or diffusion. Vesicles could also enhance local responses by targeting a subset of cells as opposed to affecting all cells in the environment.

ACPSV formation and release closely resembles microvesicle biogenesis in that vesicle formation initiates at the plasma membrane by membrane protrusion followed by vesicle dissociation in a manner that resembles cytokinesis. Although Crkl has not been implicated in microvesicle biogenesis, our data indicate that it may play an important role in ACPSV biogenesis. Interestingly, Crkl is also required for mammalian cytokinesis and its inactivation by ExoT or mutagenesis interferes with the separation of daughter cells during the abscission step in cytokinesis. Future studies are needed to determine whether Crkl functions in microvesicles biogenesis or whether alterations in Crkl (through ADP-ribosylation by ExoT or by mutagenesis) render Crkl disruptive to the process of microvesicles biogenesis.

Recently, we demonstrated that although Crkl is recruited to focal adhesion (FA) sites, it plays no role in FA assembly or FA-associated functions. This begs the question as to why Crkl is recruited to FA sites in the first place and what possible physiological role it may play in this compartment? Since all apoptotic pathways eventually converge on disruption of FA sites, as manifested by cell shrinkage, we propose that Crkl is perfectly positioned at FA sites to function as a sensor for apoptotic cell death and to initiate CPS. Without wishing to be bound by any theory, our model posits that in response to pro-apoptotic stimuli, executioner caspase-3 becomes activated. Activated caspase-3 then degrades paxillin and p103Cas (proteins that recruit and anchor Crkl at FA, thus liberating Crkl from FA to initiate CPS. We also propose that ExoT, by ADP-ribosylating Crkl blocks CPS because ADP-ribosylated Crkl is no longer competent to initiate vesicle formation.

Isolating or purifying ACPSVs from wounds. ACPSVs may be obtained from wound tissues, such as from an injured mouse. The vesicles from the injured mouse may be obtained on day 1 post-injury, weighed, cut into small pieces with a sterile scalpel, resuspended in 200 µl PBS and enzymatically dissociated in DNAse I (40 µg/ml; Sigma-Aldrich Co., St. Louis, MO)+collagenase D (2 mg/ml HBSS; Roche Diagnostics, Indianapolis, IN), and incubated such as at 37°C for 45 min with vigorous shaking every 15 min. The treated tissue may then be gently pressed through a 100 µm-cell strainer (Falcon) using a flattened pestle to remove large tissue debris. Then, the filtered flow-through may be passaged through 40-µm cell strainer without pressing. The ACPS vesicles were purified from three flow-throughs. Briefly, flowthroughs may be centrifuged at 1,500×g (1.5K) for 5 min followed by passage through 5-micron filter (Sterlitech, PES502005) to remove cell debris and apoptotic bodies, followed by centrifugation at 16,000×g (16K) for 30 min to collect ACPSVs. The presence of ACPS vesicles were confirmed by Western Blotting (probing for ACPSV marker Crkl, as in FIG. 10B) and by Differential Interference Contrast (DIC) microscopy (FIG. 10C). These vesicles may range between 0.9-1.5 micron in diameter. The amount of vesicles were determined by lipid measurements (FIG. 10A). Vesicle lipids may be extracted using the lipid quantification kit from Cell Biolabs, Inc. (Cat no. STA-613) and quantified, using Cytation3 Microplate Reader (BioTek).

In another aspect, ACPSVs may be isolated from cells grown in culture from any suitable source that will generate ACPSVs. By way of non-limiting example, ACPSVs are isolated from B16 (murine melanoma) cells. In one example, $7.5 \times 10^6$ cells were cultured in 150 mm² flasks (TPP) overnight in 25 mL of indicated media. Next day, cells were induced to undergo intrinsic apoptosis by serum-starvation. 24 to 48 h after induction of apoptosis, culture supernatants from serum-fed healthy (Mock) and apoptotic cells were collected and subjected to differential centrifugation. Protocol: Supernatants were centrifuged at 1,500×g (1.5K) for 5 min followed by passage through 5-micron filter (Sterlitech, PES502005) to remove cell debris and apoptotic bodies, followed by centrifugation at 16,000×g (16K) for 30 min to collect ACPSVs. Pellets at each centrifugation steps were re-suspended in 300 µL PBS. For functional analyses, 100 µL of PBS containing vesicles were mixed with 900 µL regular DMEM media containing 10% FBS and Penicillin-Streptomycin antibiotics and added to indicated adherent cells. The proliferation-inducing effect associated with purified ACPSVs was determined by cell counts after growing recipient cells for 24 h at 37° C. in the presence of 5% $CO_2$, using a hemocytometer after trypsin digestion. Vesicle levels were determined by lipid analysis as described, except, the lipid content in the FBS-containing media was also measured and deducted from the total lipid measurements of 16K fractions to account for the media contribution.

As shown in FIG. 11, purified or isolated ACPSVs may be used to stimulate wound healing. ACPSVs purified from B16 cell culture undergoing apoptosis as described above were assessed for their Crkl content (FIG. 11A), by DIC imaging (FIG. 11B), and for their ability to stimulate proliferation in adherent B16 cells (FIG. 11C).

When it was confirmed that these isolated ACPSVs were suitable, wounds of about 5 millimeters (mm) in diameter were opened on C57B/6 mice and these were treated topically with either a single dose of PBS (negative control) or 0.3 micrograms of purified ACPSVs. The healing was assessed by digital microscopy, as seen in FIG. 11D, and quantified, as seen in FIG. 11E. One day after treatment, the wound treated with PBS was substantially the same size as it was the previous day, while the wound treated with ACPSVs was reduced in size by about 50%. The results in FIGS. 11D and 11E demonstrate a significant but transient healing in a normal wound after one-time treatment with ACPSVs.

ACPSVs may be used to treat a number of different wound types. In one aspect, ACPSVs can be administered to a wound of a patient having a dermal or epithelial lesion or laceration to promote proliferation of cells and healing. In another aspect, ACPSVs may be used to promote healing of diabetic ulcers, or other ulcers. ACPSVs may be used in treatment of moisture-associated skin damage, pressure ulcers, abrasions, and deep tissue wounds.

Purified or isolated ACPSVs may be provided as a topical formulation. The vesicles may be suspended in a pharmaceutically acceptable carrier, excipient, or vehicle. The formulation may be in liquid, pasty or solid form, and more particularly in the form of an oil, ointment, cream, milk, powder, impregnated pad, towelette, solution, gel, spray, foam, emulsion, suspension, or lotion. In one aspect, the formulation may be a slow-release gel, which releases the ACPSVs over a course of about 2 days, or about 5 days, or about 7 days, or about 10 days, or about 14 days, or longer. The pharmaceutically acceptable carrier may include but not be limited to such substances as sterile water, olive oil, ethyl oleate, glycols such as propylene glycol, and the like.

As illustrated in the example of FIG. 11, a single dose of 0.3 microgram of ACPSV was sufficient to realize wound healing. ACPSV may be administered in a quantity from about 1 nanogram to about 10 milligrams, or about 5 nanograms to about 1 milligram, or about 10 nanograms to about 100 micrograms, or about 20 nanograms to about 50 micrograms, or about 50 nanograms to about 20 micrograms, or about 100 nanograms to about 10 micrograms, or about 150 nanograms to about 5 micrograms, or about 200 nanograms to about 2 micrograms, or about 300 nanograms to about 1 microgram, or any quantity in between.

The wound of FIG. 11 had a surface area of approximately 20 square millimeters, and 0.3 micrograms (or 300 nanograms) of ACPSVs were applied to the wound. Therefore, healing was observed when ACPSVs were administered at 15 nanograms per square millimeter ($ng/mm^2$). Therapeutically effective doses of topically administered ACPSVs may include from about 0.1 to about 1000 $ng/mm^2$, or about 0.5 to about 500 $ng/mm^2$, or about 1 to about 250 $ng/mm^2$, or about 2 to about 200 $ng/mm^2$, or about 5 to about 100 $ng/mm^2$, or about 10 to about 50 $ng/mm^2$, or about 15 to about 25 $ng/mm^2$, or any value in between.

While the example of FIG. 11 illustrates transient healing after a single treatment with ACPSVs, multiple treatments may result in sustained healing. In a prophetic example, a mouse was wounded as in FIG. 11, and treated with 0.3 microgram of ACPSVs every 24 hours. After the first administration, the wound decreased in size by 50%, as in FIG. 11. After the second dose, the wound decreased another 50%, so that it is 25% the original size. After a third dose, the wound decreased another 50%, so that it is 12.5% the original size. As can be seen in FIG. 11, the PBS treated wound is 70% of the original size, but the wound of this prophetic example would decrease to 12.5 the original size.

Further Observations

Apoptotic compensatory proliferation signaling appears to be mediated by Crkl-containing vesicles: Hela cells were transiently transfected with Crkl-EGFP expression vector. In a Crkl-GFP transfected apoptotic cell, which prior to becoming propidium iodide (PI) positive, forms and releases a Crkl-GFP containing vesicle that appears to induce proliferation in an untransfected neighboring cell upon contact. In a Crkl-GFP transfected apoptotic cell which forms and releases 3 vesicles that appear to induce proliferation in an untransfected neighboring cell upon contact. Hela cells were transiently transfected with Crkl-EGFP expression vector in the presence of Z-VAD pan-caspase inhibitor. Z-VAD inhibits apoptosis and vesicle formation in two representative Crkl-GFP transfected Hela cells.

Inactivation of Crkl by *Pseudomonas aeruginosa* ExoT/ADPRT or a null mutation in the SH2 domain of Crkl abrogates vesicle formation in apoptotic cells. HeLa cells were transiently transfected with Crkl/R38K-GFP expression vector or ExoT/ADPRT-GFP expression vector. Transfection with Crkl/R38K-GFP or ExoT/ADPRT-GFP resulted in apoptosis, as indicated by cellular uptake of PI. Unlike Crkl-GFP, Crkl/R38K-GFP or ExoT/ADPRT-GFP transfected apoptotic cells are impaired in vesicle production and in inducing CPS in surrounding bystander cells.

Exogenous vesicles induce proliferation in other cells. Crkl-containing microvesicles were purified from apoptotic MEK cells. These vesicles were then added to adherent MEK cells. A bystander recipient cell proliferates upon contacting one such vesicle.

Methods and Materials:

Cell Culture and Transient Transfection Briefly, cells were cultured in complete DMEM (Life Technologies) media supplemented with 10% FCS, 1% penicillin/streptomycin, and 1% L-glutamine at 37° C. in the presence of 5% $CO_2$. Human epithelial keratinocytes (HEK) and mouse epidermal keratinocytes (MEK) were cultured in Dermal cell growth media (ATCC PCS-200-030) supplemented with keratinocyte growth kit (ATCC PCS-200-040) at 37° C. in the presence of 5% $CO_2$. HEK cells were a generous gift from Dr. Mitchell Denning (Loyola Medicine, Chicago, IL.) MEK cells were harvested and cultured from BALB/c neonates, and cultured in Dermal cell growth media (ATCC PCS-200-030) supplemented with keratinocyte growth kit (ATCC PCS-200-040) at 37° C. in the presence of 5% $CO_2$ as described (Pirrone et al., 2004). The plasmids used in these studies were PIRES::Crkl-GFP, PIRES::Crkl/R38K-GFP, and PIRES::ExoT/ADPRT-GFP.

Cytotoxicity Measurement by Time-lapse Videomicroscopy Briefly, cells were seeded in 24-well plates (Falcon) at $6.0\times10^4$ cells per well and were grown overnight in DMEM without phenol red. These cells were then transfected with the indicated expression vectors as described. One hour after transfection, 7 μg/ml propidium iodide (PI) (Sigma) was added to the cells which were then placed on an Axiovert Z1 microscope (Zeiss) fitted with a live-imaging culture box (Pecon) maintaining 37° C. in the presence of 5% $CO_2$. Time-lapse videos were taken using AxioVision 4.2.8 software. Cytotoxicity from each frame was determined at 15-min intervals, by analyzing the PI channel in ImageJ v1.46 (National Institutes of Health) software by setting an appropriate threshold to isolate PI-positive cells.

Chemical Inhibitor Treatments: SP600125 (JNK inhibitor) and Z-VAD (pan-caspase inhibitor) were obtained from R&D Systems. These inhibitors were reconstituted in DMSO per the manufacturer's instructions, and then added to cells at 20 μM (for SP600125) or 60 M (for Z-VAD) final concentrations respectively, 2 h prior to the indicated treatments. An equivalent amount of DMSO (vehicle) was added to control cells to account for the effect of the vehicle.

Generation and Purification of ACPSVs: $7.5\times10^6$ cells were cultured in 150 $mm^2$ flasks (TPP) overnight in 25 mL of indicated media. Next day, cells were induced to undergo intrinsic apoptosis by serum-starvation, extrinsic apoptosis apoptosis by treatment with anti-Fas mAb (abcam-ab11881), or anoikis apoptosis by growing the cells detached from the surface in suspension media in Thermo Scientific Nunclon Sphera plates, in the presence or absence of Z-VAD. 24 to 48 h after induction of apoptosis, culture supernatants from serum-fed healthy (Mock) and apoptotic cells were collected and subjected to differential centrifugation. Protocol: Supernatants were centrifuged at 1,500×g (1.5K) for 5 min followed by passage through 5-micron filter (Sterlitech, PES502005) to remove cell debris and apoptotic bodies, followed by centrifugation at 16,000×g (16K) for 30 min to collect ACPSVs, followed by centrifugation at 100,000×g (100K) for 30 min for exosomes purification. Pellets at each centrifugation steps were re-suspended in 300 μL PBS. For functional analyses, 100 μL of PBS containing vesicles were mixed with 900 μL regular DMEM media containing 10% FBS and Penicillin-Streptomycin antibiotics and added to indicated adherent cells. The proliferation-inducing effect associated with each fraction was determined by cell counts after growing recipient cells for 24 h at 37° C. in the presence of 5% $CO_2$, using a hemocytometer after trypsin digestion.

Anoikis Apoptosis: To assess whether anoikis apoptosis could lead to vesicle production and CPS, $7.5\times10^6$ of indicated cells were cultured for 24 h at 37° C. in the presence of 5% $CO_2$ in suspension media in 90 $mm^2$ Nunclon Sphera surface plates (Thermo Scientific) in the presence or absence of 60 μm Z-VAD and 1% Pen-Strep antibiotics added to the appropriate media indicated for each cell line. After 24 h incubation under these conditions cells and ACPSVs were collected and processed as described.

Anti-Fas mediated extrinsic apoptosis: To induce extrinsic apoptosis, anti-Fas (anti-CD95) mAb (abcam-ab11881), was added at the final concentration of 10 mg/mL. Isoform antibody was used as control (abcam). 24 h after treatment, cytotoxicity was assessed to ensure the effectiveness of anti-Fas induced apoptosis. The ACPSVs were then purified by differential centrifugation as described and visulised by DIC.

Necrotic Cytotoxicity was induced by treatment of Hela cells with 1 µg/ml of N-methyl N'-nitro-N-nitrosoguanidine (MNNG). Briefly, To assess the production of ACPSVs in necrotic cells, $7.5 \times 10^6$ indicated cells were grown overnight in 25 ml of indicated media in 150 mm² flasks (TPP). Cells were washed four times with PBS. Cells were then treated with 1 µg/mL of N-methyl N'-nitro-N-nitrosoguanidine (MNNG) (resuspended in 25 mL of indicated media and antibiotics). Fifteen minutes after MNNG treatment, the cells were washed twice with PBS and grown in indicated media containing antibiotics at 37° C. in the presence of 5% $CO_2$. After 24 h, culture supernatants were collected and subjected to differential centrifugation as discussed above.

Cytotoxicity Assessment by Flow Cytometry Briefly, cells were collected at 24 h following cytotoxic treatments used to yield ACPSVs. Cytotoxicity was assessed using Fixable Viability Dye (eBiosciences) stain to determine the percent cell death in treated and untreated cells. The data were analyzed by flow cytometry (FACSCanto II; BD Biosciences). FACS plots were generated using FlowJo version 8.8.7.

Western Immunoblotting Briefly, cells and vesicles were lysed with 1% Triton X-100 containing a protease inhibitor cocktail (Roche Diagnostics) and Halt protease and phosphatase inhibitor (Life Technologies). Lysates were mixed with 4×SDS loading buffer and loaded onto 10% sodium dodecyl sulfate (SDS) polyacrylamide gels. After resolving, gels were transferred to polyvinylidene fluoride (PVDF) membranes, blocked with 5% milk, and probed overnight with primary antibody at 4° C. After washing, blots were probed with HRP-conjugated secondary antibody (Cell Signaling Technologies). Blots were then developed with ECL or ECL+ reagent (GE Healthcare). Films were developed using a film processor (Alphatek). The sources of antibodies (either mouse (Ms), or rabbit (Rb)) used in these studies are as follows: Crk (BD Biosciences; 610036; Ms); GAPDH (Sigma Life Sciences; G9545; Rb). HRP-linked anti-rabbit (Cell Signaling Technology; 7074) or anti-mouse (Cell Signaling Technology; 7076) IgG secondary antibodies were used.

Lipid Measurements: Vesicles lipids were extracted using the lipid quantification kit from Cell Biolabs, Inc. (Cat no. STA-613) and quantified, using Cytation3 Microplate Reader (BioTek). The lipid content of FBS-containing media was also measured and deducted from the total lipid measurements of 16K fractions to account for the media contribution.

Proliferation Assay. Cells were seeded at indicated densities (e.g., HeLa, HEK, and MEK cells at $6 \times 10^4$ cells, kidney podocytes at $1.5 \times 10^4$ cells per well) in a 24-well plate. The next day at the time of treatment with vesicles, the initial cell number per well (0 h) was determined by trypsin digestion and cell counts using a hemocytometer. Cells were then treated with ACPSVs and incubated for 24 h at 37° C. (for HeLa, HEK, and MEK cells) and 33°C (for podocytes) in the presence of 5% $CO_2$. Proliferation rates were determined blindly by cell counts determination using a hemocytometer.

Scanning Electron Microscopy (SEM) Cell and ACPSVs were grown or added on coverslips pretreated with poly-L-lysine and fixed on 4% PFA. The samples were then washed with 0.1 M sodium cacodylate buffer, post-fixed with 1% osmium tetroxide (Agar Scientific, UK), and placed in a modified histology cassette for automated gradient ethanol dehydration (25%-100% alcohol, Lynx II Automated tissue processor, Electron Microscopy Sciences) before they were critical point dried (Bal-tec850 Critical Point Dryer, Electron Microscopy Sciences). After drying cells in a precise and controlled way, cells were mounted to aluminum stubs with carbon conductive tabs (Ted Pella). Finally, the specimens were gold-coated in a sputter coater (Cressington 108auto Sputter Coater, UK), prior to view under a SEM. Micrographs were collected with the Sigma HDVP electron microscope (Zeiss) via secondary electron detector.

Animal Model of Experimental Glomerulonephritis was used to assess the occurrence of CPS in vivo. All procedures were approved by Rush University Medical Center IACUC (No: 15-069) and followed the guidelines of the NIH Guide for the Care and Use of Laboratory Animals. Nephritis was induced by nephrotoxic serum (NTS) injection. Briefly, 6 to 8 weeks old C57BL6 male mice (Jackson Laboratory) were injected retroorbitally with sheep anti-rat glomerular lysate antiserum (kindly provided by Dr. David Salant, Boston University) or control sheep IgG (Sigma) at a dose of 3 mg per mouse. Urine was collected at base line and on successive days. Urinary albumin and creatinine were measured by using mouse albumin ELISA (Bethyl Labs, E99-134), and creatinine assay (Cayman Chemical, 500701) kits. Albumin-to-Creatinine Ratio (ACR) was calculated and used as a parameter to determine proteinuria. Mice were sacrificed at 6 days after the NTS injection for histological and biochemical analyses.

Processing of glomeruli and isolation of vesicles. For processing of glomeruli and isolation of vesicles, kidneys of sheep IgG (mock)- and NTS-treated mice were minced into 1 to 3-mm tissue fragments with a scalpel blade while being maintained in ice-cold PBS. The tissue was gently pressed through a 100 µm-cell strainer (Falcon) using a flattened pestle, followed by washing with 5 ml of ice-cold HBSS (Life Technologies) to prevent the adverse effects of shear heating. Then, the filtered flow-through was passaged through 40-µm cell strainer without pressing to retain glomeruli and tubules. The flow-through was then subjected to differential centrifugation as described in Methods.

Renal parietal epithelial cells. Mouse renal parietal epithelial cells (PECs) were cultured in RPMI 1640 (Life Technologies) containing 100 U/ml penicillin and 100 µg/ml streptomycin (Life Technologies). The media was supplemented with 2% FBS and 0.1 mM sodium pyruvate (Sigma). PECs were cultured at 33° C. and 5% $CO_2$ in collagen I (BD Biosciences)-coated flasks in the presence of interferon-γ (Cell Sciences; 50 U/ml for both cells). For proliferation experiments, 25000 cells were seeded to each well of a 24-well plate and cultured at 33°C for 24 h. Then, PECs were treated with microvesicles isolated from control and NTS-treated mice, respectively. After 24 h treatment, cells were washed with PBS (Life Technologies), detached by using trypsin-EDTA (Life Technologies) for 5 min at 37° C. and harvested by centrifugation at 1200 rpm for 5 min. The cell pellet was re-suspended in the complete medium for counting and analysis.

Histopathological Evaluations Briefly, freshly harvested mouse kidneys were fixed in 4% PFA (Electron Microscopy Sciences) and embedded in paraffin. The sections were cut at 4 µm thickness and stained with hematoxylin and eosin (H&E), Periodic acid-Schiff (PAS), and Masson's Trichrome. Staining of sections with Ki-67 (Bethyl Laboratories, IHC-00375-T) was used as a marker of cell proliferation. Apoptotic cells were identified by in situ TdT-mediated dUTP nick end labeling (TUNEL) using the ApopTag Plus Peroxidase In Situ Apoptosis Detection Kit (EMD Millipore, S7101).

5-ethynyl-2'-deoxyuridine (EdU) Labeling Briefly, $8 \times 10^4$ Hela cells were seeded on coverslips, pre-treated with poly- L-lysine and human fibronectin (40 μg/mL). The following day cells were transfected as described for 24 h and then treated with 10 μM EdU for 2 h. Cells were fixed with 3.7% formaldehyde for 15 min and permeablized with 0.5% Triton X-100 for 20 min at room temperature. Next, cells were washed twice with 3% BSA in PBS, before treatment with Click-iT Plus reaction cocktail (Molecular Probes) for 30 min at room temperature protected from light. Following reaction, cells were washed once and blocked with 3% BSA for 1 h and then stained with anti-GFP antibody (Abcam; ab5450) overnight followed by anti-goat AF488 secondary antibody (Abcam; ab150129) for 1 h. Coverslips were washed three times with PBS and mounted on slides with ProLong Diamond Antifade Mountant with DAPI (Molecular Probes) and imaged using an AxioVert Z1 fluorescent microscope (Zeiss).

Proteomic Analysis: Vesicles were lysed in lysis buffer (25 mM Tris-HCl, 125 mM NaCl, 5 mM EDTA, 1% Triton X-100, pH 7.4) in the presence of a protease inhibitor mixture. The vesicle peptide content was determined by BCA assay. Filter-aided sample preparation (FASP) was applied to extract and digest proteins from vesicles. In brief, 10 μg of sample was diluted 50 times by 8 M urea in 0.1 M Tris/HCl PH 8.5 then filtered with a 0.22 UM membrane (Millipore, Billerica, MA). The flow-through was collected and transferred into a 1.5 mL MicroconYM-10 centrifugal unit (Millipore, Billerica, MA). Protein reduction, alkylation and tryptic digestion were performed step by step in the centrifugal unit. After overnight digestion at 37° C., the peptides were eluted twice with 150 μL 0.1% formic acid (FA). The concentration of proteins and peptides collected in each step was measured using a Nanodrop 1000 (Thermo Scientific, San Jose, CA). The digested peptides were then aliquoted, dried, and stored at −80° C. until further use. Sample were further fractionated using offgel pH 3-10 immobiline dry strips (GE Healthcare, Pittsburgh, PA) into 24 fractions. Fractions were desalted using Nestgroup c18 tips (Southborough, MA). Fractionated peptides were dried and re-dissolved in 0.1% FA for LC-MS/MS analysis. Fractions were run on Thermo Fisher Orbitrap Velos Pro coupled with Agilent NanoLC system (Agilent, Santa Clara, CA) over a 60 min gradient. RAW files were converted into .mgf files using MSConvert (from ProteoWizard). Database search was carried out using Mascot server (from Matrix Science). Search results from 24 runs were imported into Scaffold (Proteome Software, Portland, OR) for quantitative analysis.

Immunofluorescence (IF) static microscopy Briefly, ACPSVs, (16K fraction from serum-starved Hela cells), were seeded on poly-L-lysine and fibronectin coated coverslips, fixed with 4% PFA for 20 mins, blocked and permeabilized in permeabilization buffer (1×PBS+5% FBS+0.3% Triton™ X-100) for 60 mins at room temperature, and treated with primary antibodies for Crk (BD Transduction Laboratories-610035), Calreticulin (Abcam-ab2907), GAPDH (GenScript-A00191-40), Wnt1 (Abcam-ab85060), TGF-β (Cell signaling 3711), Actinin-4 (Abcam-ab108198), CD9 (Abcam-ab2215), or ALDH1 (Abcam-ab52492), at 1:100 or 1:200 dilutions as recommended by manufacturer in antibody dilution buffer (1×PBS/1% BSA/0.3% Triton™ X-100) overnight at 4° C. After three times wash in 1×PBS for 5 min each, coverslips were then incubated with fluorochrome-conjugated secondary antibody, Anti-mouse alexa 488 or Anit-rabbit alexa 488 procured from Jackson ImmunoResearch, for 2 h at room temperature in the dark. Coverslips were then rinsed with 1×PBS three times for 5 min each and visualized under Immunofluorescence microscope.

siRNA transfection: For JNK1/2 siRNA tranfection, Hela cells were seeded at 5×10$^5$ in 24 well plate and transfected using Opti-MEM containing 5 μl/ml Lipofectamine 2000 and 50 nM JNK1/2 or scramble siRNA control (mock) for 24 h. siRNA efficiency was determined by Western blotting using anti JNK antibody (Cell Signaling Technology; 9252).

Statistical Analyses For secondary outcomes, preplanned contrasts for between the groups at each timepoint were analyzed using a general linear model structured as an ANOVA with additional post-hoc testing using Tukey multiple comparison adjustment. Covariates were included in the model if necessary. To account for error inflation due to multiple testing, the Bonferroni stepdown adjustment was used. For experiments involving two categorical variables from a single population Chi Square ($\chi^2$) analysis was used. All analyses were performed using GraphPad Prism 6.0 software or SAS version 9.3 (SAS Inc. Cary, NC). Statistical significance threshold was set at 0.05.

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

The invention claimed is:

1. A method of treating a wound in an injured or diseased tissue, the method comprising:
administering a therapeutically effective amount dose of apoptotic compensatory proliferation signaling vesicles (ACPSVs) to the injured or diseased tissue
wherein the dose is about 15 ng/mm$^2$ to about 25 ng/mm$^2$; and
wherein the wound size is reduced by about 50%.

2. The method of claim 1, wherein the ACPSVs are purified ACPSVs.

3. The method of claim 1, wherein the injured tissue comprises one of an epithelial lesion and an epithelial laceration.

4. The method of claim 1, wherein the diseased tissue comprises a diabetic ulcer.

5. The method of claim 1, wherein the ACPSVs are administered as a topical formulation.

6. The method of claim 5, wherein the topical formulation is selected from the group consisting of an oil, an ointment, a cream, a milk, a powder, an impregnated pad, a towelette, a solution, a gel, a spray, a foam, an emulsion, a suspension, and a lotion.

7. The method of claim 1, wherein administering comprises treating the injured or diseased tissue with a single dose of ACPSVs.

8. The method of claim 1, wherein administering comprises treating the injured or diseased tissue with multiple doses of ACPSVs.

9. A pharmaceutical composition for promoting proliferation of cells in an injured or diseased tissue, the pharmaceutical composition comprising a therapeutically effective amount of apoptotic compensatory proliferation signaling vesicles (ACPSVs) and at least one pharmaceutically acceptable carrier, wherein the ACPSVs are purified ACPSVs.

10. The pharmaceutical composition of claim 9, wherein the purified ACPSVs are isolated from mouse tissue, rat tissue, primate tissue, or human tissue.

11. The pharmaceutical composition of claim 9, wherein the purified ACPSVs are isolated from cultured cells.

12. The pharmaceutical composition of claim 9, wherein the pharmaceutical composition is a topical formulation.

13. The pharmaceutical composition of claim 12, wherein the topical formulation is selected from the group consisting of an oil, an ointment, a cream, a milk, a powder, an impregnated pad, a towelette, a solution, a gel, a spray, a foam, an emulsion, a suspension, and a lotion.

14. The pharmaceutical composition of claim 13, wherein the topical formulation comprises a slow-release gel.

15. The pharmaceutical composition of claim 9, wherein the pharmaceutical composition contains an amount of ACPSVs effective to treat the injured or diseased tissue with a single dose.

16. The pharmaceutical composition of claim 9, wherein the pharmaceutical composition contains an amount of ACPSVs effective to treat the injured or diseased tissue with multiple doses.

17. The pharmaceutical composition of claim 9, comprising about 1 picogram to about 100 grams of ACPSVs per dose.

* * * * *

UNITED STATES PATENT AND TRADEMARK OFFICE
CERTIFICATE OF CORRECTION

PATENT NO. : 12,076,341 B2
APPLICATION NO. : 17/252782
DATED : September 3, 2024
INVENTOR(S) : Sasha Shafikhani Page 1 of 1

It is certified that error appears in the above-identified patent and that said Letters Patent is hereby corrected as shown below:

In the Claims
Column 24, Line 35, delete "amount".

Signed and Sealed this
First Day of April, 2025

Coke Morgan Stewart
*Acting Director of the United States Patent and Trademark Office*